US012616420B2

(12) United States Patent
Zaides et al.

(10) Patent No.: US 12,616,420 B2
(45) Date of Patent: *May 5, 2026

(54) COMPUTING LOCAL PROPAGATION VELOCITIES FOR CARDIAC MAPS

(71) Applicant: BIOSENSE WEBSTER (ISRAEL) LTD., Yokneam (IL)

(72) Inventors: Leonid Zaides, Atlit (IL); Elad Nakar, Timrat (IL); Eliyahu Ravuna, Kiryat Ata (IL); Yoav Benaroya, Kfar Saba (IL); Fady Massarwi, Baka al Gharbiyya (IL); Jonathan Yarnitsky, Haifa (IL); Lior Greenbaum, Zoran (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 957 days.

This patent is subject to a terminal disclaimer.

(21) Appl. No.: 17/672,774

(22) Filed: Feb. 16, 2022

(65) Prior Publication Data

US 2022/0370016 A1     Nov. 24, 2022

Related U.S. Application Data

(60) Provisional application No. 63/192,221, filed on May 24, 2021, provisional application No. 63/192,231, filed on May 24, 2021.

(51) Int. Cl.
*A61B 5/00*        (2006.01)
*G06F 18/2135*        (2023.01)
(52) U.S. Cl.
CPC .......... *A61B 5/7264* (2013.01); *A61B 5/7203* (2013.01); *A61B 5/7228* (2013.01); *A61B 5/7275* (2013.01); *G06F 18/2135* (2023.01)

(58) Field of Classification Search
CPC .......................... A61B 5/7264; G06F 18/2135
(Continued)

(56) References Cited

U.S. PATENT DOCUMENTS 5,391,199 A     2/1995  Ben Haim
5,443,489 A     8/1995  Ben Haim
(Continued)

FOREIGN PATENT DOCUMENTS

CN        109953755 A    7/2019
EP          2627243 A1    8/2013
(Continued)

OTHER PUBLICATIONS

European Search report for corresponding EPA No. 22174860.1 dated Oct. 28, 2022.
(Continued)

*Primary Examiner* — Nadia A Mahmood
(74) *Attorney, Agent, or Firm* — Clayton, McKay & Bailey, PC

(57) ABSTRACT

A method includes obtaining multiple local activation times (LATs) at different respective measurement locations on an anatomical surface of a heart. The method further includes computing respective directions of electrical propagation at one or more sampling locations on the anatomical surface, by, for each sampling location, selecting a respective subset of the measurement locations for the sampling location, constructing a set of vectors, each of at least some of the vectors including, for a different respective measurement location in the subset, three position values derived from respective position coordinates of the measurement location and an LAT value derived from the LAT at the measurement location, and computing the direction of electrical propagation at the sampling location based on a Principal Component Analysis (PCA) of a 4×4 covariance matrix for the set
(Continued)

of vectors. The method further includes indicating the directions of electrical propagation on a display.

20 Claims, 14 Drawing Sheets

(58) Field of Classification Search
  USPC .......................................................... 600/509
  See application file for complete search history.

(56)                    References Cited

U.S. PATENT DOCUMENTS

| | | | |
|---|---|---|---|
| 5,558,091 | A | 9/1996 | Acker |
| 5,944,022 | A | 8/1999 | Nardella |
| 5,983,126 | A | 11/1999 | Wittkampf |
| 6,177,792 | B1 | 1/2001 | Govari |
| 6,456,864 | B1 | 9/2002 | Swanson |
| 6,690,963 | B2 | 2/2004 | Ben Haim |
| 6,788,967 | B2 | 9/2004 | Ben Haim |
| 7,536,218 | B2 | 5/2009 | Govari |
| 8,456,182 | B2 | 6/2013 | Bar-Tal |
| 9,380,953 | B2 | 7/2016 | Houben et al. |
| 2010/0268059 | A1 | 10/2010 | Ryu |
| 2014/0067279 | A1 | 3/2014 | George et al. |
| 2015/0196770 | A1 | 7/2015 | Cappelaere |
| 2015/0208938 | A1 | 7/2015 | Houben et al. |
| 2017/0311833 | A1 | 11/2017 | Afonso et al. |
| 2021/0093217 | A1 | 4/2021 | Shariat et al. |
| 2021/0228133 | A1 | 7/2021 | Bhogu |
| 2022/0142578 | A1 | 5/2022 | Nakar et al. |

FOREIGN PATENT DOCUMENTS

| | | |
|---|---|---|
| EP | 3721796 A1 | 10/2020 |
| EP | 3733060 A1 | 11/2020 |
| WO | 0115088 A1 | 3/2001 |
| WO | WO2001015011 A2 | 3/2001 |
| WO | WO2017192775 A1 | 11/2017 |

OTHER PUBLICATIONS

Cantwell, Chris D., et al., "Techniques for automated local activation time annotation and conduction velocity estimation in cardiac mapping," Computers in biology and medicine 65 (2015): 229-242.

Roney, Caroline H., et al., "An automated algorithm for determining conduction velocity, wavefront direction and origin of focal cardiac arrhythmias using a multipolar catheter," 2014 36th Annual International Conference of the IEEE Engineering in Medicine and Biology Society, IEEE, 2014.

European Search Report for corresponding EPA No. 22174769.4 dated Sep. 9, 2022.

Office Action for JP Application No. 2022-083625 dated Dec. 5, 2025.

121

RECOMPUTE PROPAGATION DIRECTIONS  ∽128

123

ANY SAMPLING POINTS NOT SELECTED YET?    NO

YES

SELECT NEXT SAMPLING POINT  ∽125

COMPUTE AVERAGE POSITION OF POINTS IN NEIGHBORHOOD OF SAMPLING POINT  ∽122

COMPUTE PROJECTION OF SAMPLING POINT ONTO LINE ORIENTED IN PROPAGATION DIRECTION AT SAMPLING POINT AND PASSING THROUGH AVERAGE POSITION  ∽124

MOVE SAMPLING POINT TOWARD PROJECTION  ∽126

130

YES    PERFORM ANOTHER ITERATION?

NO

END

*FIG. 10*

COMPUTING LOCAL PROPAGATION VELOCITIES FOR CARDIAC MAPS

CROSS-REFERENCE TO RELATED APPLICATIONS

The present application claims the benefit of U.S. Provisional Application 63/192,221, entitled "Computing local propagation velocities for cardiac maps," filed May 24, 2021, whose disclosure is incorporated herein by reference, and U.S. Provisional Application 63/192,231, entitled "Computing local propagation velocities in real-time," filed May 24, 2021, whose disclosure is incorporated herein by reference.

FIELD OF THE DISCLOSURE

The present disclosure is related to the field of cardiac mapping.

BACKGROUND

The local activation time (LAT) at any portion of cardiac tissue is the difference between (i) the time at which the tissue becomes electrically activated during any cardiac cycle, and (ii) a reference time during the same cycle. The reference time may be set, for example, to a point in the QRS complex of a body-surface electrocardiogram (ECG) recording.

US Patent Application Publication 2015/0196770 describes a system including an active medical device with means for delivering defibrillation shocks, means for continuous collection of the patient current cardiac activity parameters. and evaluator means with neuronal analysis comprising a neural network with at least two layers. The neural network comprises upstream three neural sub-networks receiving the respective parameters divided into separate sub-groups corresponding to classes of arrhythmogenic factors, and downstream an output neuron coupled to the three sub-networks and capable of outputting an index of risk of ventricular arrhythmia. The risk index is compared with a given threshold, to enable or disable at least one function of the device in case of crossing of the threshold.

US Patent Application Publication 2010/0268059 describes a method including accessing cardiac information acquired via a catheter located at various positions in a venous network of a heart of a patient where the cardiac information comprises position information, electrical information and mechanical information, mapping local electrical activation times to anatomic positions to generate an electrical activation time map, mapping local mechanical activation times to anatomic positions to generate a mechanical activation time map, generating an electromechanical delay map by subtracting local electrical activation times from corresponding local mechanical activation times, and rendering at least the electromechanical delay map to a display.

Cantwell, Chris D., et al., "Techniques for automated local activation time annotation and conduction velocity estimation in cardiac mapping," Computers in biology and medicine 65 (2015): 229-242 surveys algorithms designed for identifying local activation times and computing conduction direction and speed.

Roney, Caroline H., et al., "An automated algorithm for determining conduction velocity, wavefront direction and origin of focal cardiac arrhythmias using a multipolar catheter," 2014 36th Annual International Conference of the IEEE Engineering in Medicine and Biology Society, IEEE, 2014 describes automated algorithms for identifying conduction velocity from multipolar catheter data with any arrangement of electrodes, whilst providing estimates of wavefront direction and focal source position.

BRIEF DESCRIPTION OF THE DRAWINGS

The present disclosure will be more fully understood from the following detailed description of examples thereof, taken together with the drawings, in which:

FIG. 10 is a flow diagram for an iterative condensing algorithm, in accordance with some examples of the present disclosure;

DETAILED DESCRIPTION OF EXAMPLES

Overview

Figure 1:
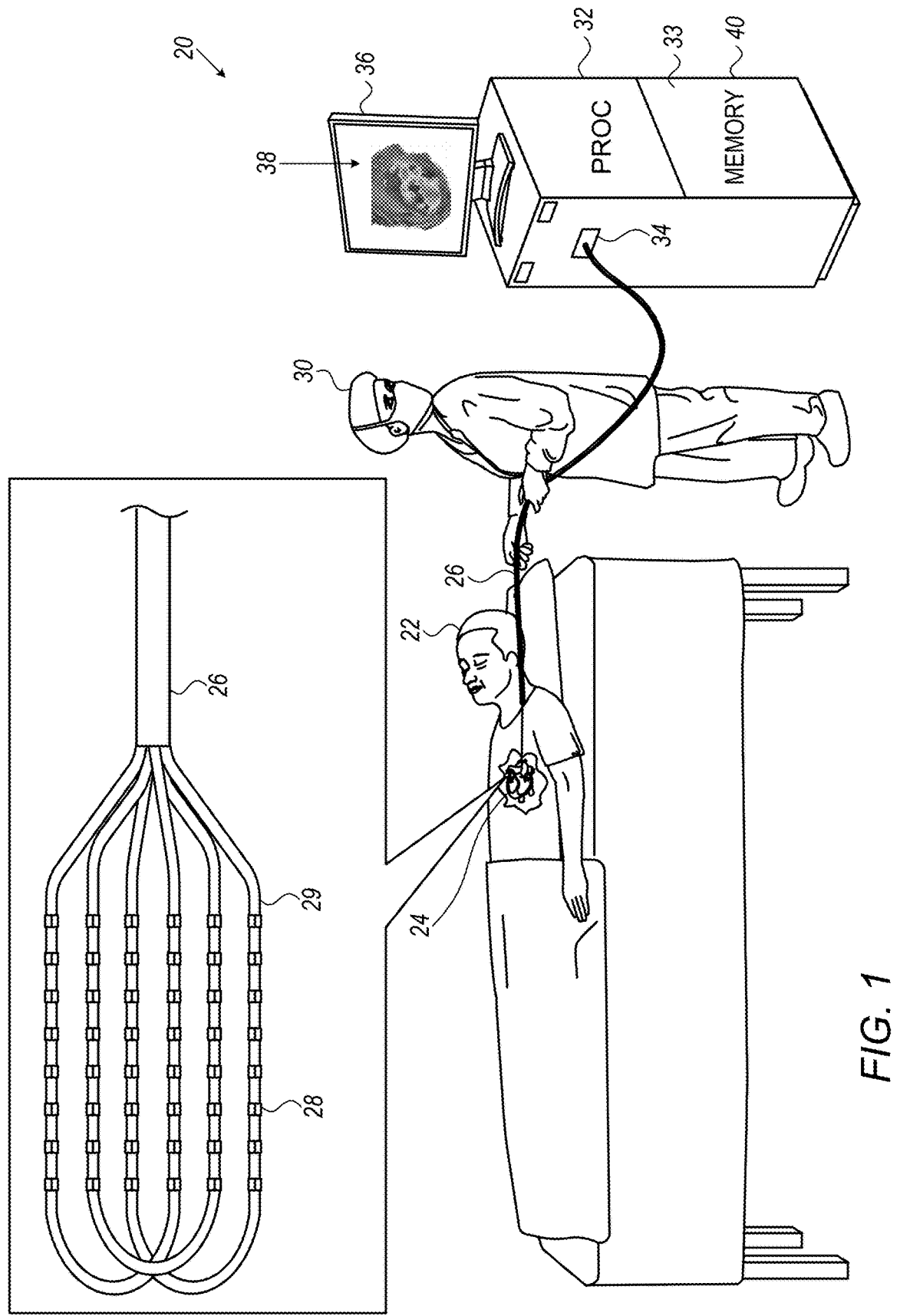
FIG. 1 is a schematic illustration of a system for electro-anatomical mapping, in accordance with some examples of the present disclosure.

During an electroanatomical mapping, an intrabody probe, which comprises a plurality of electrodes at its distal end, is moved along a surface of a heart. Based on bioelectrical signals acquired from the surface by the electrodes, various electrical properties of the surface, such as the LATs at various locations on the surface, are estimated. (The process of estimating a LAT based on one or more acquired signals is also referred to hereinbelow as a "measurement" of the LAT.)

Examples of the present disclosure provide algorithms for accurately computing propagation velocities at small spatial resolutions, based on the LATs. Examples of the present disclosure further provide techniques for visually indicating the propagation velocities to a physician, so as to facilitate proper diagnosis and treatment.

In particular, for each "sampling location" on the surface at which a velocity is to be computed, a computer processor selects a suitable set of nearby "measurement locations" at which respective LATs were measured. Advantageously, this set excludes any measurement locations separated from the sampling location by electrically-inactive tissue. Subsequently, a respective four-dimensional vector is constructed for each of the measurement locations in the set (and, provided an LAT was measured at the sampling location, the sampling location itself). Each vector includes three position values derived from the position coordinates of the measurement location, along with an LAT value derived from the LAT measured at the measurement location.

Subsequently, the processor performs a Principal Component Analysis (PCA) of a 4×4 covariance matrix for the vectors, and computes the propagation velocity at the sampling location based on the PCA. For example, the processor may compute the direction of propagation by projecting the principal component of the covariance matrix onto the three position dimensions. The processor may then project the measurement locations in the set onto a line passing through the sampling location and oriented in the propagation direction. Next, the processor may compute a regression function approximating the relationship between the projections and the corresponding LATs. Finally, the processor may estimate the magnitude of the velocity (i.e., the speed of propagation) as the slope of this function.

In some examples, the propagation velocities are computed following a full mapping of the cardiac surface in which the probe is moved across the surface so as to measure a large number of LATs at respective measurement locations. In particular, subsequently to the mapping, the processor constructs a model of the surface, in which respective measurement points on the surface of the model correspond to the measurement locations. Next, the processor designates, on the model surface, a plurality of sampling points, which correspond to respective sampling locations on the anatomical surface. The processor then computes a propagation velocity at each sampling location, based on a suitable set of measurement locations.

In such examples, subsequently to computing the propagation velocities, the processor typically displays the model with overlaid markers indicating one or more properties of the propagation velocities. For example, at each sampling point, the processor may place a marker oriented in the direction of the propagation velocity at the sampling point. Sampling points at which the magnitude of the propagation velocity is below a predefined threshold may be marked differently from other sampling points, such that the physician may readily identify areas of slow conduction.

(It is noted that in the description of such examples herein, a reference to a point on the surface of the model may be substituted for a reference to the location on the anatomical surface corresponding to the point, and vice versa. For example, an LAT measured at a particular measurement location may be said to be associated with the measurement point on the model surface corresponding to the measurement location. Similarly, the (x, y, z) position coordinates of a location on the anatomical surface may be referred to as the position coordinates of the point on the model surface corresponding to the location.)

Alternatively or additionally, propagation velocities may be computed in real-time, during the mapping procedure. In particular, following each round of LAT measurements (which are typically conducted once per cardiac cycle), the processor may iterate through the measurement locations (i.e., the locations of the electrodes). For each measurement location, the processor may identify a suitable set of neighboring measurement locations. The processor may then construct respective vectors for the measurement locations, perform a PCA of the corresponding covariance matrix, and compute the propagation velocity based on the PCA.

In such examples, typically, the processor repeatedly refreshes a display of an icon of the distal end of the probe, which comprises the electrodes, with overlaid markers indicating one or more properties of the propagation velocities. For example, at each electrode, the processor may place a marker oriented in the direction of the propagation velocity at the electrode. As in the case of the non-real-time display, the properties of the markers may be varied as a function of the propagation speeds.

Another challenge, when performing electroanatomical mapping, is that a measured bipolar voltage may falsely indicate electrically-inactive tissue on the cardiac surface, in the event that the pair of electrodes used to measure the bipolar voltage are oriented with respect to one another perpendicularly to the local propagation direction.

To address this challenge, examples of the present disclosure use the aforementioned real-time computations to choose pairs of electrodes that are most closely aligned with the local propagation directions. Bipolar voltages between the chosen pairs of electrodes are associated with the model of the cardiac surface, while other bipolar voltages are omitted from the model.

Examples of the present disclosure further provide an enhanced LAT computation based on multiple bipolar voltages.

System Description

Reference is initially made to FIG. 1, which is a schematic illustration of a system 20 for electroanatomical mapping, in accordance with some examples of the present disclosure.

In FIG. 1, a physician 30 is shown moving the distal end of a probe 26 along an anatomical surface of a portion of a heart 24 of a subject 22, such as an endocardial surface of a chamber of the heart. While the distal end of probe 26 is moved along the surface, a processor 32 belonging to system 20 uses electrodes 28 at the distal end of the probe to measure respective local activation times (LATs) at various measurement locations on the surface. In particular, as electrodes 28 acquire electrogram signals at the measurement locations, the processor processes these signals so as to compute the LATs. Typically, the electrogram signals include both unipolar signals, i.e., signals between the electrodes and a common reference electrode, and bipolar voltages, i.e., voltages between pairs of adjacent electrodes.

(Typically, for cases in which the mapping is performed during the occurrence of a cyclic arrhythmia, calculating an LAT comprises two steps. First, a standard LAT calculation is performed, as described above in the Background. Subsequently, in the event that the absolute value of the LAT is greater than p*CL, where CL is the length of each cycle in the cyclic arrhythmia and p≤0.5 is specified by the physician, CL is added to or subtracted from the LAT such that the absolute value of the LAT is less than p*CL.)

In some examples, the distal end of probe 26 comprises a plurality of parallel splines 29, each spline 29 comprising a linear arrangement of electrodes. Alternatively, a grid of electrodes may be arranged on a balloon, an expandable printed circuit board (PCB), or any other suitable structure at the distal end of the probe.

Typically, the processor is contained within a console 40, comprising an electrical interface 34 such as a port or socket. The probe is connected to console 40 via electrical interface 34, such that electrogram signals acquired by the electrodes are received, by the processor, via electrical interface 34. Typically, the signals are carried through the probe, along wires, in analog form, and the console further comprises analog-to-digital (A/D) conversion circuitry configured to convert the signals to digital form for processing by processor 32.

During the mapping procedure, the processor tracks the location of the distal end of the probe. Based on the tracking and on the electrogram signals received from the electrodes, the processor may construct a digital model 38 of the portion of the heart, also referred to herein as a "map." The processor may further store the model in a memory 33, comprising any suitable type of volatile or non-volatile memory, and/or display model 38 on a display 36.

In some examples, to facilitate the aforementioned tracking, the distal end of the probe comprises one or more electromagnetic sensors. In the presence of a generated magnetic field, these sensors output, to the processor (e.g., via electrical interface 34), signals indicating the respective locations of the sensors. Such location-tracking techniques are disclosed, for example, in U.S. Pat. Nos. 5,391,199, 5,443,489, and 6,788,967 to Ben-Haim, in U.S. Pat. No. 6,690,963 to Ben-Haim et al., in U.S. Pat. No. 5,558,091 to Acker et al., and in U.S. Pat. No. 6,177,792 to Govari, whose respective disclosures are incorporated herein by reference.

In other examples, impedance is measured between electrodes 28 (and/or other electrodes at the distal end of the probe) and electrode patches coupled to the body of subject 22. Based on the impedance measurements, the processor ascertains the locations of the electrodes. Typically, in such examples, the processor utilizes a location map calibrated, in advance, using electromagnetic sensors, as described, for example, in U.S. Pat. No. 7,536,218 to Govari et al. and U.S. Pat. No. 8,456,182 to Bar-Tal et al., whose respective disclosures are incorporated herein by reference.

In yet other examples, currents are passed between the electrode patches. Based on the voltages measured at electrodes 28, the processor ascertains the locations of the electrodes. Such techniques are described, for example, in U.S. Pat. No. 5,983,126 to Wittkampf, U.S. Pat. No. 6,456, 864 to Swanson, and U.S. Pat. No. 5,944,022 to Nardella, whose respective disclosures are incorporated herein by reference.

System 20 may further comprise one or more input devices, such as a keyboard, a mouse, or a touch screen belonging to display 36. Physician 30 may use the input devices to enter any suitable inputs, such as any of the various thresholds described below.

In general, processor 32 may be embodied as a single processor, or as a cooperatively networked or clustered set of processors. The functionality of processor 32 may be implemented solely in hardware, e.g., using one or more fixed-function or general-purpose integrated circuits, Application-Specific Integrated Circuits (ASICs), and/or Field-Programmable Gate Arrays (FPGAs). Alternatively, this functionality may be implemented at least partly in software. For example, processor 32 may be embodied as a programmed processor comprising, for example, a central processing unit (CPU) and/or a Graphics Processing Unit (GPU). Program code, including software programs, and/or data may be loaded for execution and processing by the CPU and/or GPU. The program code and/or data may be downloaded to the processor in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

Computing Propagation Velocities

Figure 2:
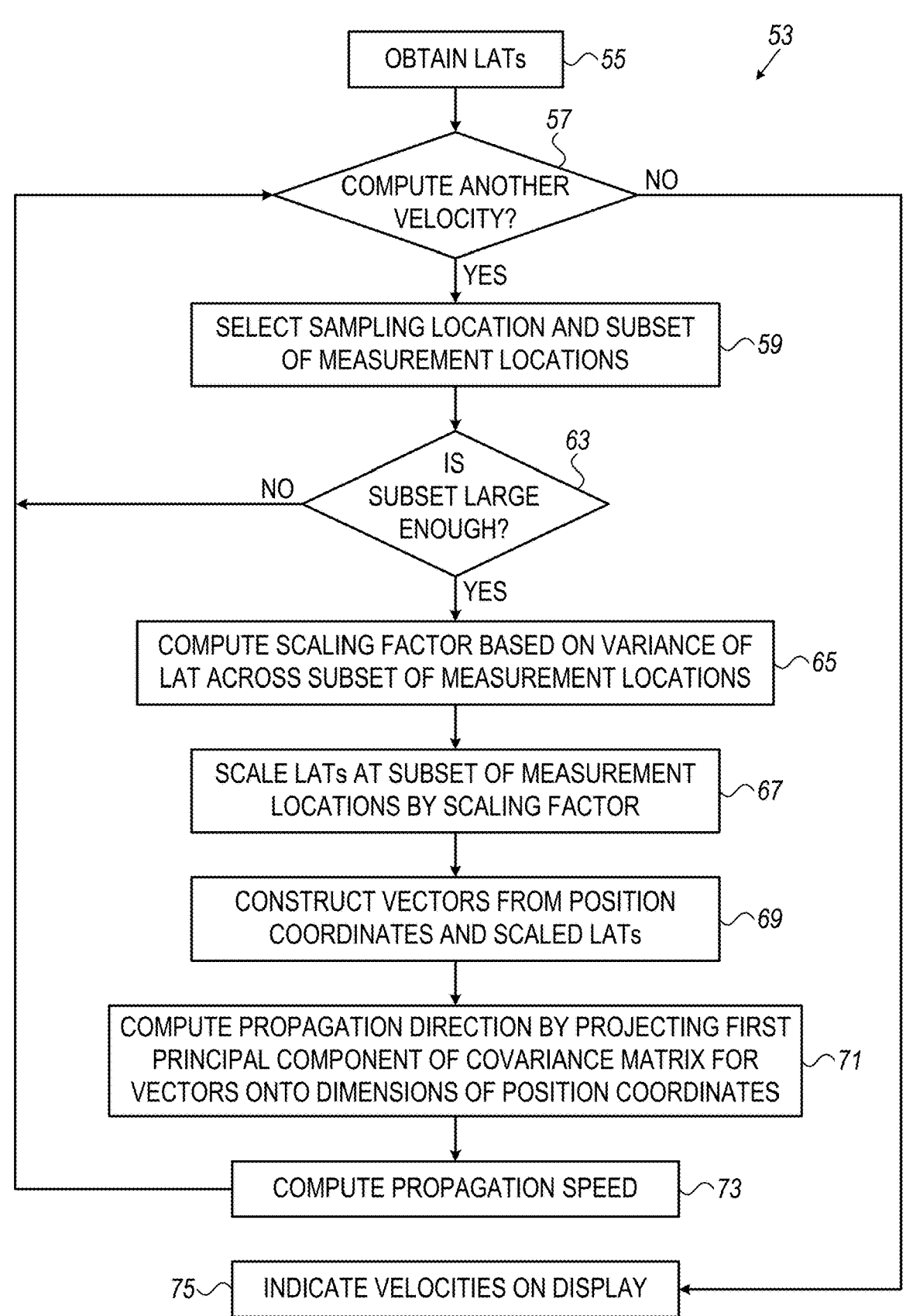
FIG. 2 is a flow diagram for an algorithm for computing and displaying propagation velocities, in accordance with some examples of the present disclosure.

Reference is now made to FIG. 2, which is a flow diagram for an algorithm 53 for computing and displaying propagation velocities, in accordance with some examples of the present disclosure. Processor 32 (FIG. 1) may execute algorithm 53 either in real-time, while electrogram signals are acquired, or subsequently to the acquisition.

Algorithm 53 begins with an LAT-obtaining step 55, at which the processor obtains multiple LATs at different respective measurement locations on an anatomical surface of heart 24 (FIG. 1). For example, the processor may obtain the LATs by calculating the LATs, as described above with reference to FIG. 1, or—when executing the algorithm after the mapping—by reading the LATs from memory 33 (FIG. 1) or from an external storage device, such as a flash drive.

Subsequently to obtaining the LATs, the processor, at an assessing step 57, assesses whether to attempt to compute a propagation velocity for at least one sampling location. If yes, the processor, at a selecting step 59, selects a sampling location for the velocity calculation, along with a subset of the measurement locations whose LATs may be used for the calculation. (Selecting step 59 is further described below with reference to FIG. 4.) Next, at a subset-size-assessing step 63, the processor assesses whether the subset of measurement locations is large enough for the calculation, i.e., whether the subset includes a threshold number of measurement locations.

Provided that the subset of measurement locations is large enough, the processor constructs a set of vectors corresponding to the subset of measurement locations. Each of the vectors includes, for a different respective measurement location in the subset, three position values derived from respective position coordinates of the measurement location, and an LAT value derived from the LAT measured at the measurement location. (Thus, each of the vectors is four-dimensional.) Alternatively, if the subset is not large enough, the processor returns to assessing step 57.

Typically, to construct the set of vectors, the processor first computes, at a scaling-factor-computing step 65, a scaling factor based on the variance of the LATs across the subset of the measurement locations. Subsequently, for each of the measurement locations in the subset, the processor scales, by the scaling factor, either the position coordinates of the measurement location or the LAT at the measurement location, and constructs the vector corresponding to the measurement location from the scaled parameter. (The same parameter is scaled for each of the measurement locations.)

For example, the processor may first scale the LATs by the scaling factor, at a LAT-scaling step 67. Subsequently, the processor, at a vector-constructing step 69, may construct the vectors from the position coordinates and the scaled LATs. For example, for any particular measurement location, the processor may construct the vector [x0 y0 z0 s*L0], where (x0, y0, z0) are the position coordinates of the measurement location, L0 is the LAT at the measurement location, and s is the scaling factor.

For examples in which the LAT is scaled, the scaling factor is typically a ratio between a target LAT variance $$\sigma_T^2$$

and the actual variance $$\sigma_A^2$$

of the LATs across the subset of measurement locations, this ratio typically being greater than one. For examples in which the position coordinates are scaled instead, the scaling factor is typically $$\sigma_A^2/\sigma_T^2,$$

this ratio typically being less than one.

In some examples, the target LAT variance is computed per a predefined (increasing) function of the predefined distance D0 described below with reference to FIG. 3. For example, the target LAT variance may equal $c*D0^2$, where c is a constant between 5 and 10, for example. In other examples, the spatial variance of the subset of measurement locations is computed for the three x-, y-, and z-axes, and the target LAT variance is computed as a multiple of the largest spatial variance.

Subsequently to constructing the set of vectors, the processor computes the direction of electrical propagation at the selected sampling location based on a Principal Component Analysis (PCA) of the 4×4 covariance matrix for the set of vectors. For example, the processor may project the first principal component of the covariance matrix (a four-dimensional vector) onto respective dimensions of the position coordinates (thus yielding a three-dimensional vector).

By way of illustration, Table 1 below shows a set of eight vectors constructed from experimental data. (In this particular example, the LATs were scaled up by a factor of six.)

TABLE 1

| X | Y | Z | LAT |
|---|---|---|---|
| 4.875 | 50 | −0.375 | 113.4 |
| 7.125 | 50 | −1.125 | 129.6 |
| 7.125 | 50 | −0.375 | 129.6 |
| 7.125 | 50 | 1.125 | 129.6 |
| 7.125 | 50 | 1.875 | 129.6 |
| 9.375 | 50 | −0.375 | 145.8 |
| 9.375 | 50 | 0.375 | 145.8 |
| 9.375 | 50 | 1.125 | 145.8 |

Table 2 below shows the covariance matrix for this set of vectors:

8

TABLE 2

| | | | |
|---|---|---|---|
| 2.215 | 0 | 0.264 | 15.947 |
| 0 | 0 | 0 | 0 |
| 0.264 | 0 | 0.905 | 1.898 |
| 15.947 | 0 | 1.898 | 114.818 |

The first principal component of this matrix is [−0.138 −1.165*10⁻¹⁶ −0.016−0.990], and the projection of the first principal component onto the XYZ space is [−0.138 −1.165*10⁻¹⁶ −0.016], which, expressed as a unit direction vector, is [0.993 8.406*10⁻¹⁶ 0.119].

The first principal component of this matrix is $[-0.138\ -1.165*10^{-16}\ -0.016-0.990]$, and the projection of the first principal component onto the XYZ space is $[-0.138\ -1.165*10^{-16}\ -0.016]$, which, expressed as a unit direction vector, is $[0.993\ 8.406*10^{-16}\ 0.119]$.

Following the computation of the propagation direction, the processor computes the propagation speed at the selected sampling location, at a speed-computing step 73. (Speed-computing step 73 is described below with reference to FIG. 3.) The processor then returns to assessing step 57.

Further to ascertaining, at assessing step 57, that no further velocities are to be computed, the processor, at a displaying step 75, indicates the velocities on display 36 (FIG. 1), as further described below with reference to FIGS. 9A-B and 12.

In alternate examples, the processor computes the directions of electrical propagation without computing the speeds, and indicates the directions on the display without indicating the speeds.

Figure 3:
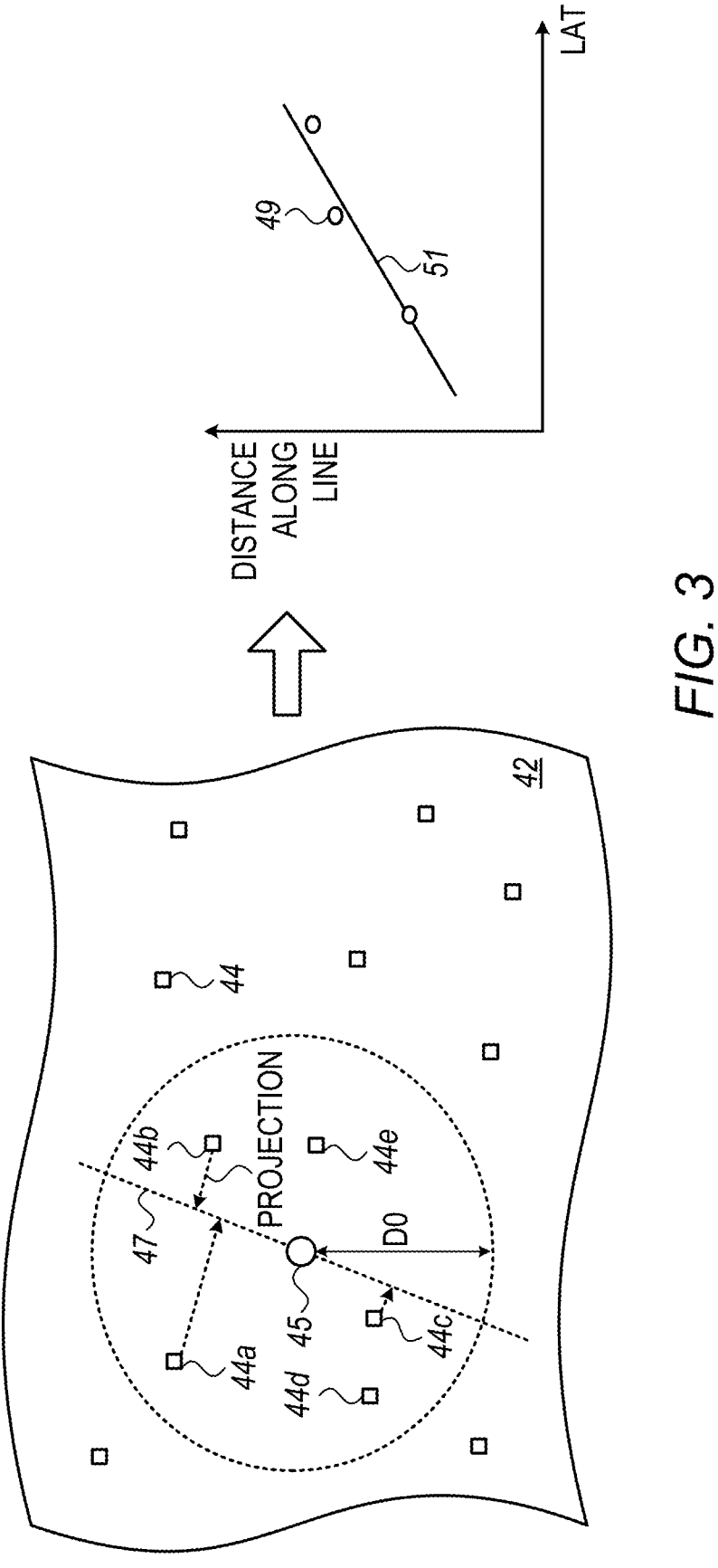
FIG. 3 is a schematic illustration of a propagation-velocity computation, in accordance with some examples of the present disclosure.

For further details regarding some examples of algorithm 53, reference is now additionally made to FIG. 3, which is a schematic illustration of a propagation-velocity computation, in accordance with some examples of the present disclosure.

FIG. 3 shows a plurality of measurement locations 44 on an anatomical surface 42. Subsequently to obtaining the LATs at measurement locations 44 by performing LAT-obtaining step 55, the processor executes the subsequent steps of algorithm 53 as described above. Thus, for example, in performing selecting step 59, the processor may first select a sampling location 45 on anatomical surface 42. (As further described below with reference to FIG. 5, sampling location 45 does not necessarily coincide with one of measurement locations 44.) Subsequently, the processor may identify those of measurement locations 44 that are within a predefined distance D0 of sampling location 45, and then select the subset of measurement locations from the identified measurement locations, as further described below with reference to FIG. 6. For example, per the example in FIG. 3, the processor selects, of the measurement locations within distance D0 of sampling location 45, measurement locations 44a, 44b, and 44c, without selecting measurement locations 44d and 44e.

For instances in which algorithm 53 is not performed in real-time, as further described below with reference to FIGS. 5-10, D0 is typically between 6 and 12 mm. For instances in which algorithm 53 is performed in real-time, as further described below with reference to FIGS. 11-12, D0 is typically between 4 and 8 mm, such as between 5 and 7 mm. More generally, D0 may be a function of the density of the measurement locations.

(It is noted that, although appearing two-dimensional in FIG. 3, anatomical surface 42 is three-dimensional. Thus, typically, the processor uses a geodesic distance measure for computing distances along the surface.)

In some examples, if the processor subsequently ascertains at subset-size-assessing step 63 that the subset is too small, the processor may increase distance D0 one or more times (up to a predefined maximum), repeating the selection each time.

Upon ascertaining that the subset is large enough, the processor computes the propagation direction as described above. Subsequently, the processor computes the propagation speed at speed-computing step 73.

In some examples, to compute the propagation speed, the processor first projects the subset of measurement locations onto a hypothetical line 47 passing through sampling location 45 and oriented in the direction of electrical propagation at the sampling location. The processor then computes the respective distances along line at which the projections lie. Next, the processor defines a group of points 49, each of which includes, for a different respective measurement location in the subset, (i) the distance along the line at which the projection of the measurement location lies, and (ii) the LAT at the measurement location. Subsequently, the processor fits a regression function 51 to points 49 (or to a subset of points 49 near the LAT measured at, or—as described below with reference to FIG. 5—interpolated for, sampling location 45), and then computes the speed of electrical propagation as the slope of function 51.

For example, function 51 may be a line, and the speed of electrical propagation may be computed as the slope of the line. Alternatively, the function may be a polynomial of order two or higher, a spline function, or any other suitable type of function. In such examples, the speed may be computed as the slope of the function at the LAT measured at or interpolated for sampling location 45. Alternatively, the processor may compute the speed of electrical propagation in any other suitable way. For example, the processor may compute a 2×2 covariance matrix for points 49, and then compute the speed of electrical propagation based on the first principal component of this matrix. Alternatively, the processor may divide the projections into two groups: a first group at one side of sampling location 45, and a second group at the other side of sampling location 45. (Thus, per the example in FIG. 3, the first group would include the projections of measurement locations 44a and 44b, while the second group would include the projection of measurement location 44c.) Subsequently, the processor may compute the respective centers of mass of each group, each center of mass being the average location of the projections in the group. The speed may then be computed as the slope of a line passing between the two centers of mass.

Figure 4:
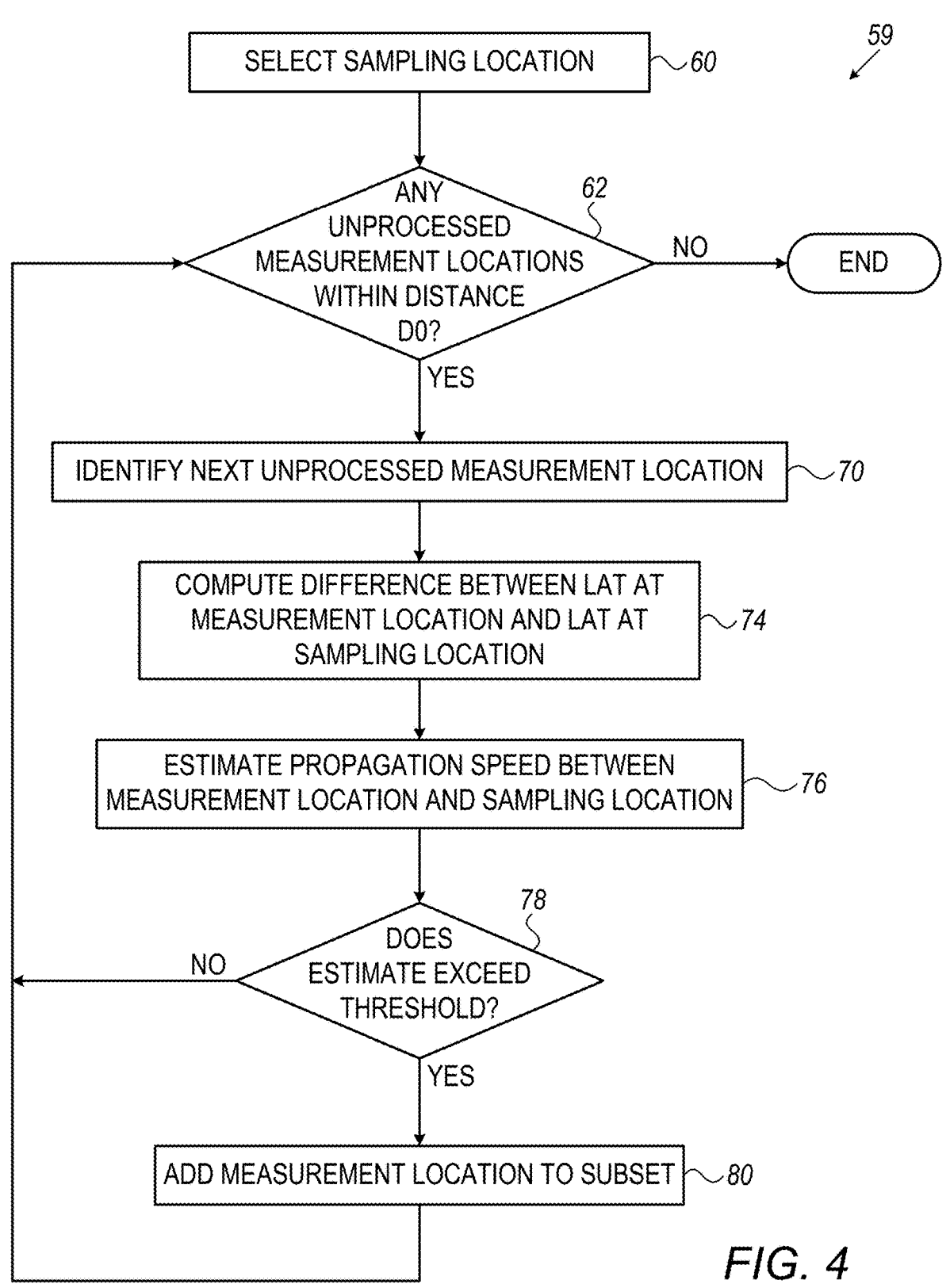
FIG. 4 is a flow diagram for a selecting step shown in FIG. 2, in accordance with some examples of the present disclosure.

For further details regarding selecting step 59, reference is also made to FIG. 4, which is a flow diagram for selecting step 59, in accordance with some examples of the present disclosure.

Selecting step 59 begins with a sampling-location-selecting step 60, at which the processor selects a sampling location 45. Subsequently, the processor, at a checking step 62, checks whether any measurement locations within distance D0 of the sampling location have yet to be processed. If yes, the processor, at a measurement-location-identifying step 70, identifies one of these measurement locations for processing. Subsequently, the processor, at a difference-computing step 74, computes the difference between the LAT at the measurement location and the LAT at the sampling location.

Based on the computed LAT difference, the processor, at a speed-estimating step 76, computes a propagation-speed estimate, which estimates the propagation speed between the sampling location and the measurement location. Typically, this estimate is the quotient of the LAT difference and the distance between the sampling location and the measurement location, which the processor computes at checking step 62.

Subsequently, the processor checks, at a checking step 78, whether the propagation-speed estimate exceeds a predefined speed-estimate threshold $v_{T1}$. If yes, the measurement location is added to the selected subset of measurement locations, at a subset-augmenting step 80. Otherwise, the measurement location is not added to the subset. (In the event that the propagation-speed estimate does not exceed $v_{T1}$, there is likely a block between the sampling location and the measurement location, such that adding the measurement location to the subset would render inaccurate the subsequent computation of the propagation velocity.)

Subsequently to subset-augmenting step 80, or if the propagation-speed estimate does not exceed $v_{T1}$, the processor returns to checking step 62. Upon ascertaining that all measurement locations within distance D0 were processed, selecting step 59 ends.

Computation and Display Based on a Model

Figure 5:
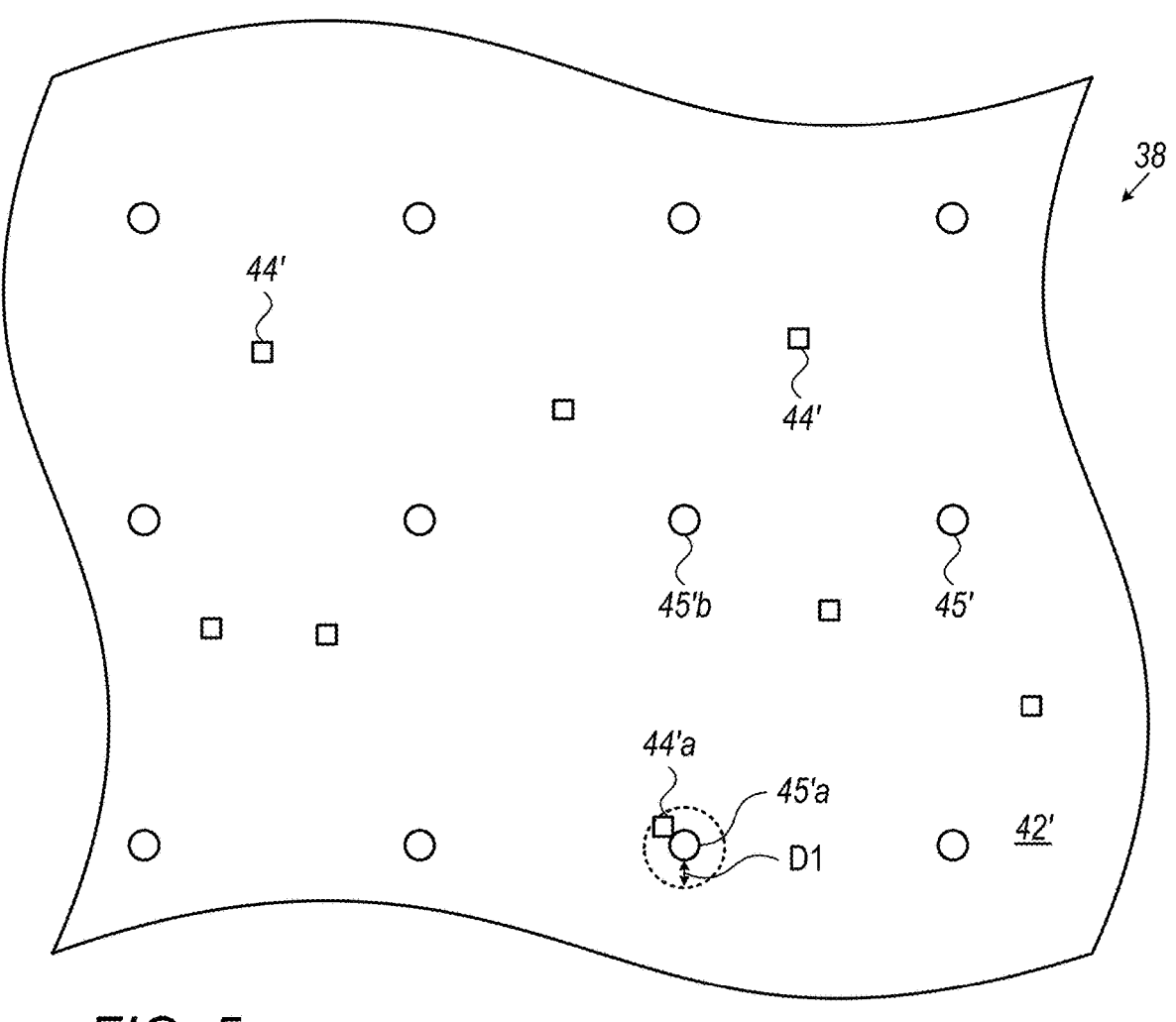
FIG. 5 is a schematic illustration of a surface of a digital model, in accordance with some examples of the present disclosure.

Reference is now made to FIG. 5, which is a schematic illustration of a surface 42' of digital model 38, in accordance with some examples of the present disclosure.

In some examples, the processor constructs model 38 from a point cloud corresponding to multiple locations of the distal end of probe 26 (FIG. 1) on anatomical surface (FIG. 3), typically by performing a triangular tessellation of the point cloud. Measurement locations 44 (FIG. 3) correspond to different respective measurement points 44' on surface 42' of model 38. (It is noted that since surface 42' is a "best fit" that does not necessarily pass through every point in the point cloud, some measurement points 44' may be computed by projecting a point from the point cloud onto surface 42'.)

In such examples, the computation of propagation velocities may be performed following the construction of the model. In particular, the processor may designate a plurality of sampling points 45' on surface 42', e.g., by uniformly sampling the surface. Subsequently, the processor may iterate through the sampling points when performing algorithm 53 (FIG. 2). In particular, at assessing step 57 of algorithm 53, the processor may assess whether any sampling points have yet to be processed. If yes, the processor may perform an example of selecting step 59 referred to hereinbelow as a model-based selecting step 59'. Subsequently, provided the selected subset of measurement locations is large enough, the processor may compute the propagation velocity for the sampling point, as described above with reference to FIGS. 2-3.

Figure 6:
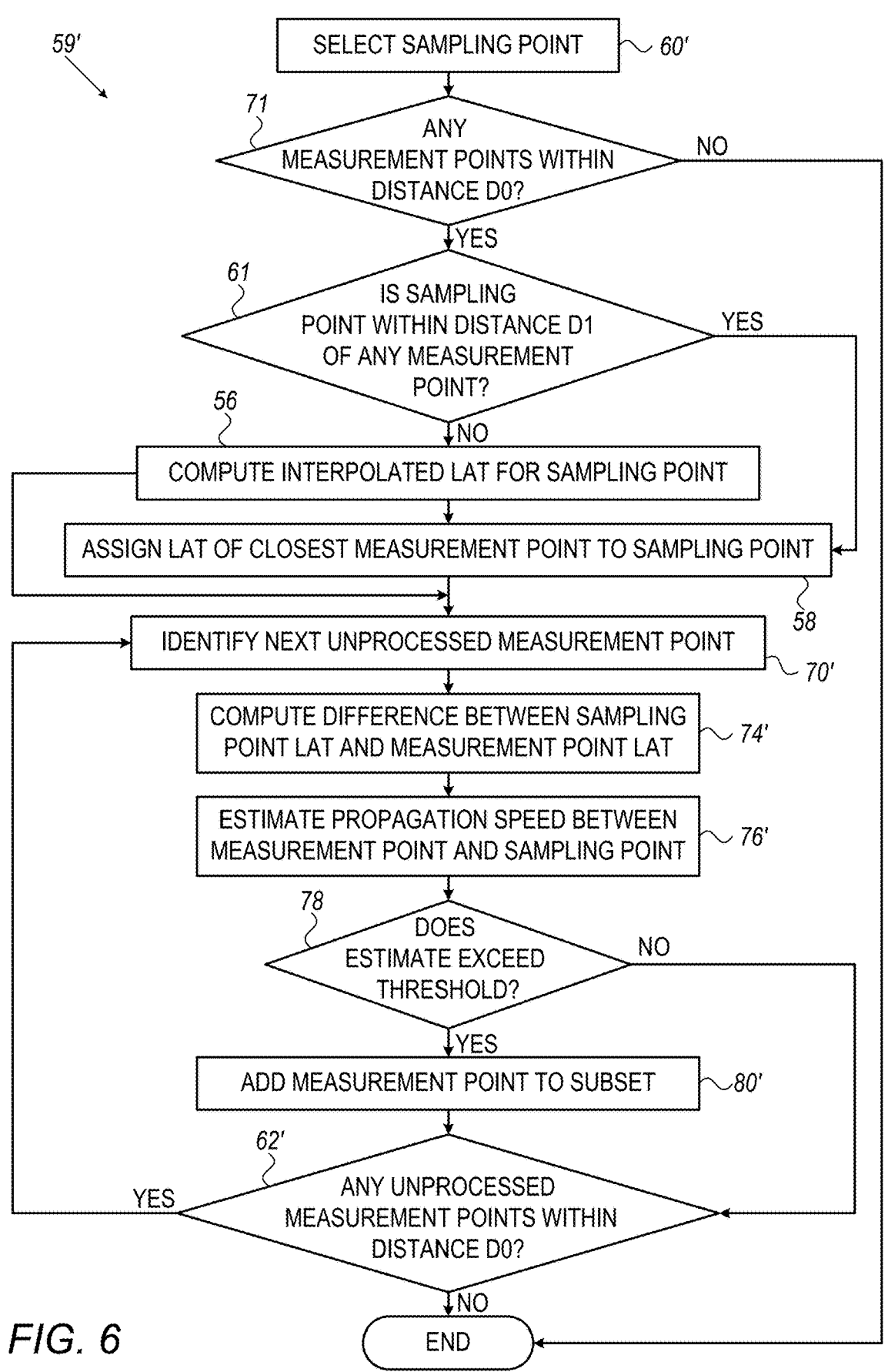
FIG. 6 is a flow diagram for an instance of the selecting step shown in FIG. 2, in accordance with some examples of the present disclosure.

Reference is now further made to FIG. 6, which is a flow diagram for model-based selecting step 59', in accordance with some examples of the present disclosure.

Model-based selecting step 59' begins with a sampling-point-selecting step 60', at which the processor selects a sampling point.

In some examples, following sampling-point-selecting step 60', the processor checks, at a checking step 71, whether any measurement points are within distance D0 of the selected sampling point. If not, model-based selecting step 59' ends. Otherwise, the processor checks, at a checking step 61, whether the selected sampling point is within a predefined distance D1 of any of the measurement points 44'. Typically, D1 is much smaller than D0, e.g., 0.5 mm or less.

If the sampling point is within D1 of at least one measurement point, the processor considers the sampling point to coincide with the closest measurement point. (In other words, the processor considers the sampling location corresponding to the sampling point to coincide with the closest measurement location for which a LAT was obtained.)

Hence, the processor, at a LAT-assigning step 58, assigns the LAT of the closest measurement point to the sampling point.

Alternatively, if no measurement point is within D1 of the sampling point, the processor, at an interpolating step 56, computes an interpolated LAT for the sampling point by interpolating at least some of the LATs associated with those of the measurement points identified at checking step 71, as further described below with reference to FIGS. 7-8, and assigns the interpolated LAT to the sampling point.

Thus, for example, as shown in FIG. 5, a first sampling point 45'a may be assigned the LAT of the closest measurement point 44'a, whereas an interpolated LAT may be computed for a second sampling point 45'b, which is not sufficiently close to any measurement points.

Subsequently to assigning an LAT to the sampling point, the processor, at a measurement-point-identifying step 70', identifies an unprocessed measurement point for processing. Subsequently, the processor, at a difference-computing step 74', computes the difference between the LAT associated with the sampling point and the LAT associated with the measurement point. Based on the computed LAT difference, the processor, at a speed-estimating step 76', estimates the propagation speed between the measurement point and the sampling point. Subsequently, the processor checks, at a checking step 78, whether the propagation-speed estimate exceeds the predefined speed-estimate threshold $v_{T1}$. If yes, the measurement point is added to the selected subset of measurement points, at a subset-augmenting step 80'. Otherwise, the measurement point is not added to the subset.

Subsequently to subset-augmenting step 80', or if the propagation-speed estimate does not exceed $v_{T1}$, the processor checks, at a checking step 62', whether any more unprocessed measurement point are within distance D0. Upon ascertaining that all measurement points within distance D0 were processed, selecting step 59' ends.

In some examples, to compute an interpolated LAT at interpolating step 56, the processor first clusters those of the measurement points within distance D0 of the sampling point into one or more clusters such that, for each of the clusters, for each pair of measurement points in the cluster, a propagation-speed estimate, which estimates a propagation speed between the pair of measurement points, exceeds a predefined speed-estimate threshold $v_{T2}$, which may be different from $v_{T1}$. The processor then identifies one of the clusters, based on respective distances between the sampling point and the clusters. The processor then computes the interpolated LAT for the sampling point as a weighted average of those of the LATs associated, respectively, with at least some of the measurement points in the identified cluster.

Figure 7:
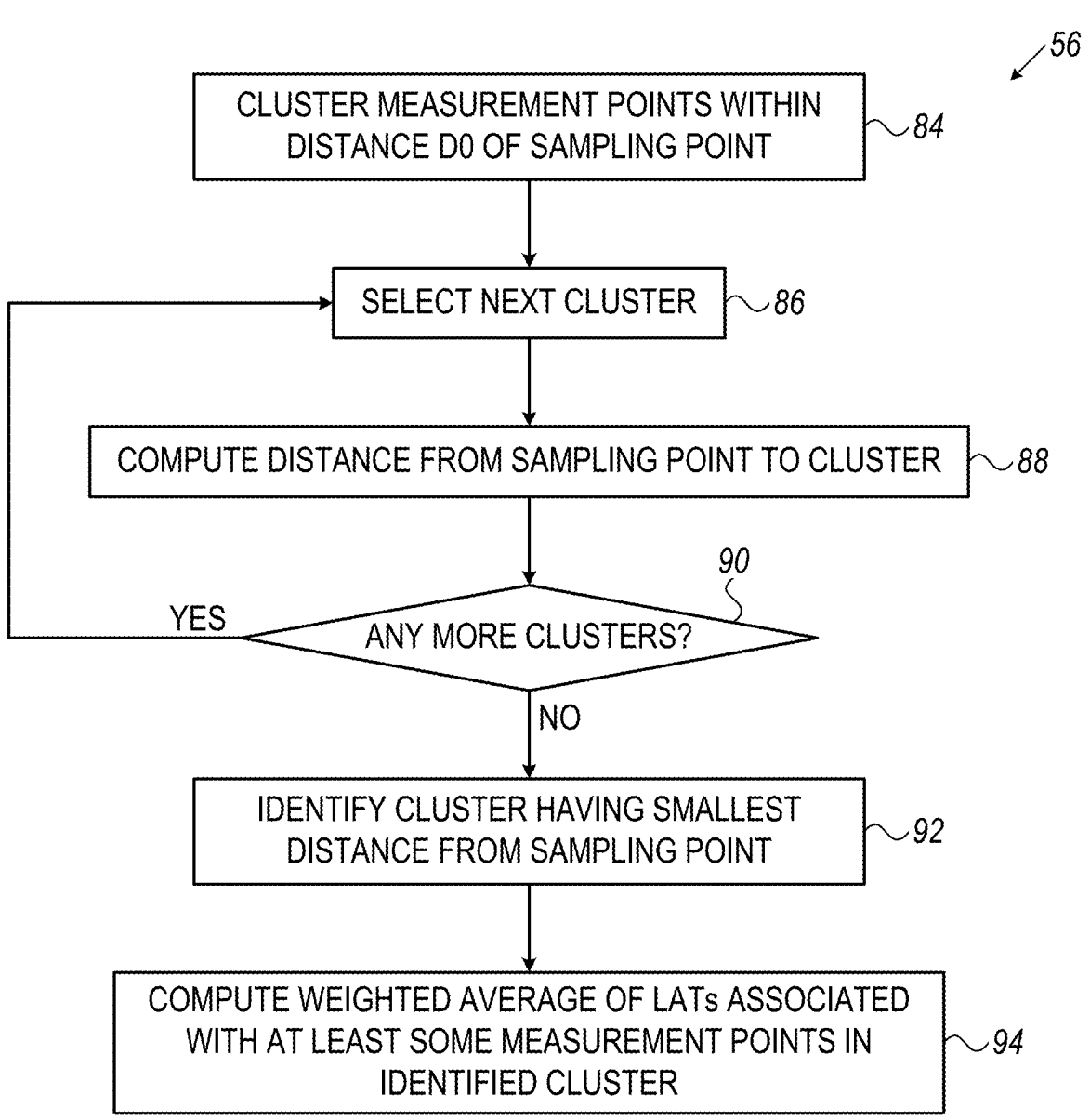
FIG. 7 is a flow diagram for an interpolating step shown in FIG. 6, in accordance with some examples of the present disclosure.

In this regard, reference is now made to FIG. 7, which is a flow diagram for interpolating step 56, in accordance with some examples of the present disclosure.

Interpolating step 56 begins with a clustering step 84, at which the processor clusters those of the measurement points within distance D0 of the sampling point, as described above. An example of clustering step 84 is described below with reference to FIG. 8.

Following clustering step 84, each cluster is selected at a first cluster-selecting step 86. For each selected cluster, the processor, at a distance-computing step 88, computes the distance from the sampling point to the cluster. In general, any suitable definition of this distance may be used. For example, the processor may compute the distance as the average distance between the sampling point and the N measurement points in the cluster that are closest to the sampling point, N being two, three, or four, for example.

Subsequently, the processor checks, at a checking step 90, whether any more clusters have yet to be selected. If yes, the processor returns to cluster-selecting step 86. Otherwise, at a cluster-identifying step 92, the processor identifies the cluster having the smallest distance from the sampling point. Subsequently to identifying the cluster, the processor, at a weighted-averaging step 94, computes the interpolated LAT as a weighted average of the LATs associated with at least some of the measurement points in the identified cluster, such as the N measurement points closest to the sampling point. Typically, the weight $w_i$ for the LAT of each $i^{th}$ measurement point is equal to $$\left(\frac{1}{d_i}\right) \Big/ \left(\sum \frac{1}{d_j}\right),$$

where $d_i$ is the distance of the $i^{th}$ measurement point from the sampling point.

By virtue of performing the interpolation as described above, the processor generally refrains from basing the interpolated LAT on a measurement point that is separated from the sampling point by electrically-inactive tissue.

Figure 8:
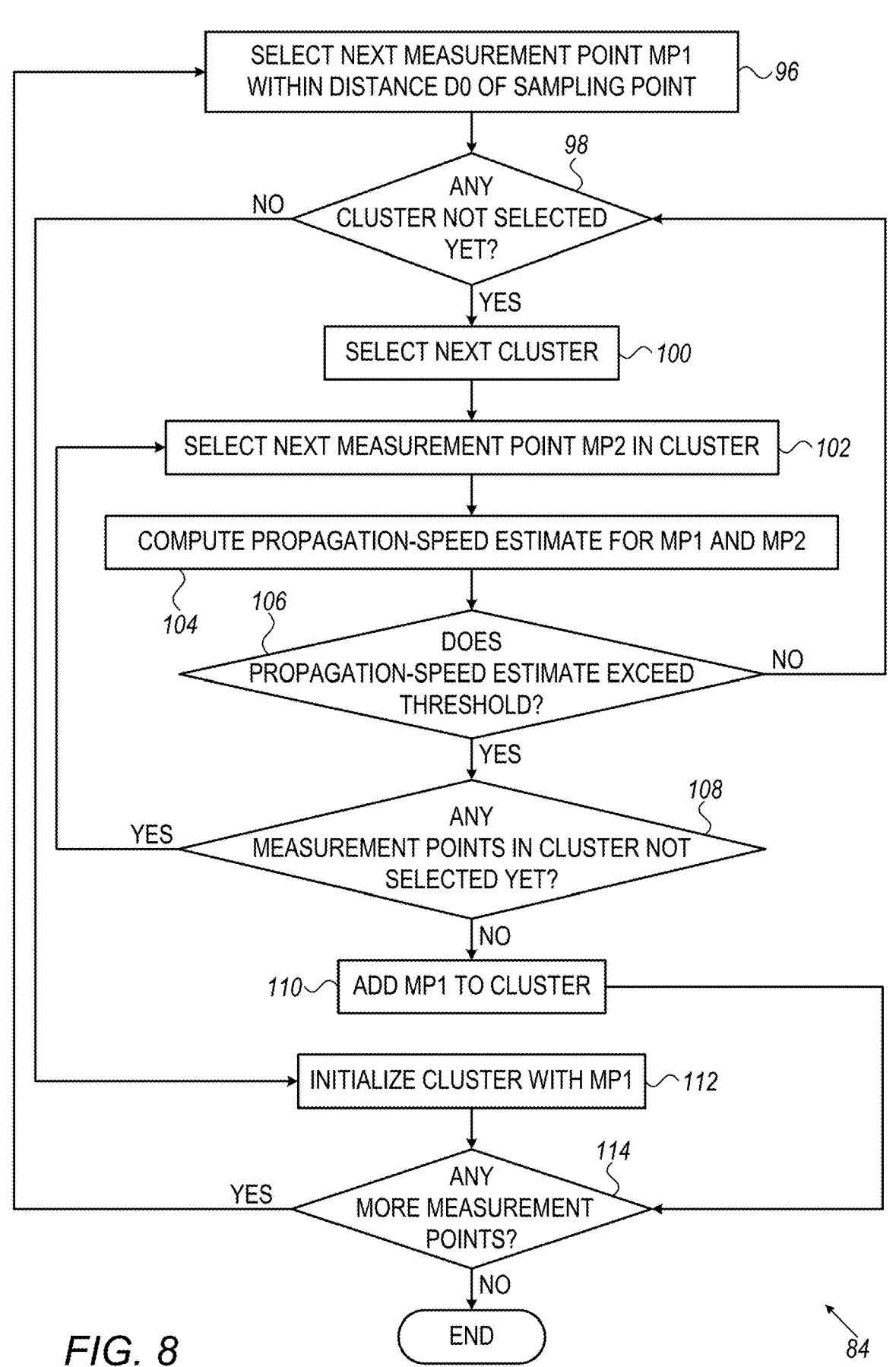
FIG. 8 is a flow diagram for a clustering step shown in FIG. 7, in accordance with some examples of the present disclosure.

Reference is now made to FIG. 8, which is a flow diagram for clustering step 84, in accordance with some examples of the present disclosure.

To perform clustering step 84, the processor, at a first measurement-point-selecting step 96, iteratively selects each measurement point within distance D0 of the sampling point. For each selected measurement point, referred to in FIG. 8 as "MP1," the processor checks, at a checking step 98, whether any clusters exist and have not yet been selected. If not, the processor, at a cluster-initializing step 112, initializes a cluster with MP1. Otherwise, the processor, at a second cluster-selecting step 100, selects the next cluster that has not been selected yet.

Subsequently to selecting a cluster, the processor, at a second measurement-point-selecting step 102, selects one of the measurement points, referred to in FIG. 8 as "MP2," in the cluster. Next, at another speed-estimating step 104, the processor computes a propagation-speed estimate, which estimates the propagation speed between MP1 and MP2. The processor then checks, at a checking step 106, whether the propagation-speed estimate exceeds the threshold $v_{T2}$. If not, the processor returns to checking step 98. Otherwise, the processor checks, at a checking step 108, whether any measurement points in the cluster have not been selected yet. If there is at least one measurement point that has not yet been selected, the processor returns to second measurement-point-selecting step 102 and selects the next measurement point MP2. Otherwise, the processor adds MP1 to the cluster at a cluster-growing step 110.

Following cluster-growing step 110 or cluster-initializing step 112, the processor checks, at a checking step 114, whether any measurement points within distance D0 of the sampling point have not yet been selected. If yes, the processor returns to first measurement-point-selecting step 96 and selects the next measurement point MP1. Otherwise, clustering step 84 ends.

Figure 9A:
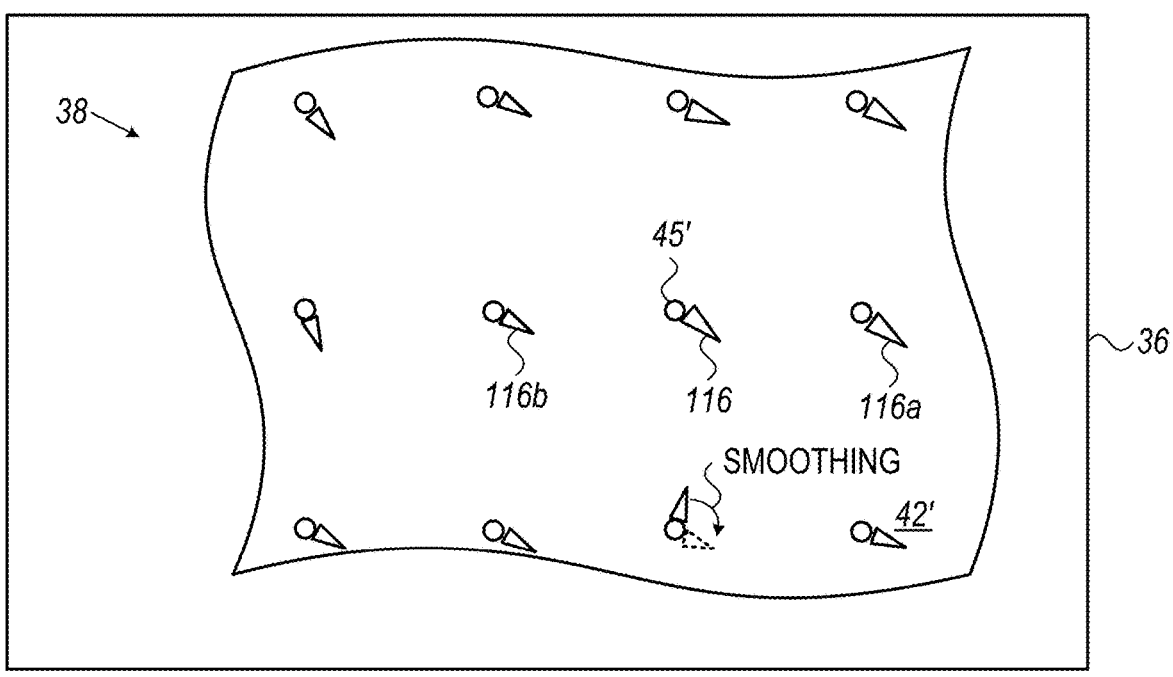
FIGS. 9A-B are schematic illustrations of a displayed model, in accordance with some examples of the present disclosure.

Reference is now made to FIG. 9A, which is a schematic illustration of a displayed model, in accordance with some examples of the present disclosure.

Subsequently to computing the propagation velocities, the processor displays model 38 (in particular, model surface 42') with respective markers 116 overlaying the model at sampling points 45' and oriented in the directions of electrical propagation, respectively. (For better visibility, each marker 116 may be slightly offset from its sampling point, e.g., in a direction parallel to model surface 42'.) Each marker 116 may have any suitable shape, such as the arrowhead shape shown in FIG. 9A or a full arrow shape. Optionally, additional markers, such as the circles shown in FIG. 9A, may mark the positions of the sampling points on model surface 42'.

In addition to orienting markers 116 so as to indicate the directions of electrical propagation, the processor may vary at least one other property—such as the color, shape, length, or thickness—of the markers in accordance with the speeds of electrical propagation. For example, the property may be set to a first value for each speed that does not exceed a predefined speed threshold $v_{T3}$ (or, as described immediately below, does not exceed $v_{T3}$ with a threshold measure of confidence), and to a second value otherwise. As a specific example, a thicker marker 116a may be placed at each sampling point for which the speed does not exceed $v_{T3}$, while thinner markers 116b may be placed at the other sampling points. Thicker markers 116a thus indicate areas of slow conduction on the anatomical surface, which may be of interest to the physician.

In some examples, a measure of confidence is calculated for each speed that does not exceed the speed threshold $v_{T3}$. If the measure of confidence exceeds a predefined confidence threshold, the marker property is set to the first value; otherwise, the property is set to the second value. The measure of confidence may be defined, for example, as the ratio of (i) the number of neighboring sampling points at which the speed does not exceed the speed threshold, to (ii) the total number of neighboring sampling points. A neighboring sampling point S2 of a sampling point S1 may be defined, for example, as any sampling point that is within a predefined distance of S1, provided that the propagation-speed estimate between S1 and S2 exceeds $v_{T1}$.

In some examples, the model is displayed so as to further indicate other properties of the anatomical surface. For example, model surface 42' may be colored so as to indicate the LATs on the anatomical surface.

In some examples, prior to visually indicating the directions of electrical propagation, the processor smooths the directions of electrical propagation. For example, the processor may perform a Laplacian smoothing, whereby, during each $i^{th}$ iteration of the smoothing, the unit propagation-direction vector V[i] at each sampling point is computed as $\alpha*V[i-1]+(1-\alpha)*V_A[i]$, where $V_A$ is the average unit propagation-direction vector for the neighbors of the sampling point. (As described above, a neighbor may be any other sampling point that is within a predefined distance of the sampling point, provided that the propagation-speed estimate between the two points exceeds $v_{T1}$.) FIG. 9A illustrates an example result of such a smoothing operation, by showing one of the markers reoriented in approximately the same direction as that of its neighbors.

Figure 9B:
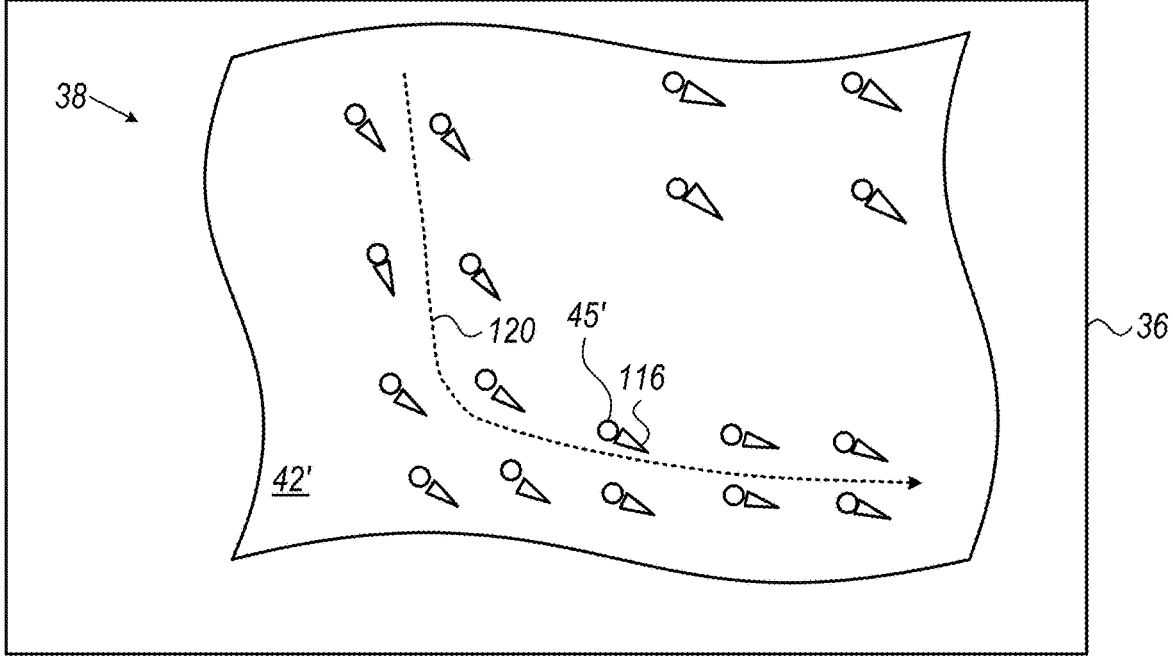

Reference is now made to FIG. 9B, which is another schematic illustration of a displayed model, in accordance with some examples of the present disclosure.

In some examples, alternatively or additionally to smoothing the directions of electrical propagation, the processor, prior to displaying the model with the overlaid markers, condenses the sampling points such that the sampling points approximately follow one or more average propagation pathways 120. The processor thus facilitates interpretation of the displayed model by the physician.

Typically, the condensing is performed by executing an iterative algorithm. During each iteration of the algorithm, the processor recomputes the directions of electrical propagation, and then shifts the sampling points toward each other in response to the directions of electrical propagation.

In this regard, reference is now made to FIG. 10, which is a flow diagram for one such iterative condensing algorithm 121, in accordance with some examples of the present disclosure.

At the start of each iteration of algorithm 121, the processor recomputes the propagation directions at a recomputing step 128. Typically, in this step, the computation of the propagation velocities is performed as described above with reference to FIG. 2, with the neighbors of the sampling point substituting for the subset of measurement points. For example, for each sampling point, the processor may (i) construct respective vectors for the sampling point and its neighbors, (ii) perform a PCA of the corresponding 4×4 covariance matrix, and (iii) compute the propagation direction based on the PCA, e.g., by projecting the first principal component of the covariance matrix onto the respective dimensions of the position coordinates.

Subsequently, the processor checks, at a checking step 123, whether any sampling points have yet to be selected. If yes, the processor selects the next sampling point at a sampling-point-selecting step 125. Next, the processor, at an average-position-computing step 122, computes the average position of the points in the neighborhood of the sampling point. These points include the selected sampling point along with the neighbors of the selected sampling point. As described above with reference to FIG. 9A, a neighbor may be defined as any sampling point that is within a predefined distance of the selected sampling point, provided that the propagation-speed estimate between the two sampling points exceeds the speed-estimate threshold $v_{T1}$.

Following average-position-computing step 122, the processor, at a projection-computing step 124, computes the projection of the sampling point onto a line oriented in the direction of propagation at the sampling point and passing through the average position. The processor then moves the sampling point toward the projection, at a point-moving step 126. For example, during each $i^{th}$ iteration of the algorithm, the processor may compute the new position P[i] of the sampling point as $\alpha*P[i-1]+(1-\alpha)*Pp[i]$, where Pp is the projection of the sampling point. Subsequently to moving the sampling point, the processor returns to checking step 123.

Upon ascertaining, at checking step 123, that all the sampling points have been selected during the present iteration, the processor assesses, at an assessing step 130, whether to perform another iteration. If yes, the processor performs the next iteration of the algorithm; otherwise, the execution of the algorithm ends.

In general, assessing step 130 may be based on any suitable criteria. For example, the processor may terminate execution of the algorithm if, during the present iteration, none of the sampling points moved by more than a predefined threshold distance, or if a predefined maximum number of iterations have been performed.

Real-Time Computation and Display

Figures 11, 12:
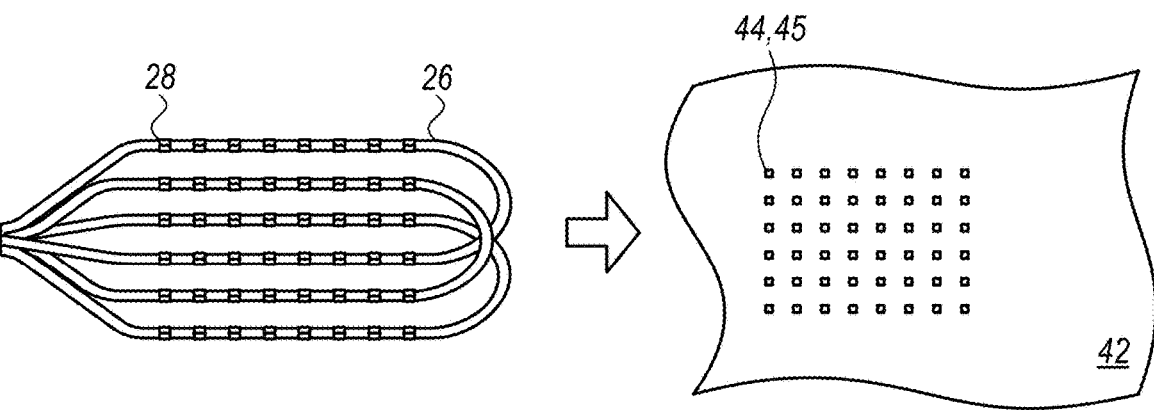
FIG. 11 is a schematic illustration of a probe and an anatomical surface, in accordance with some examples of the present disclosure.
FIG. 12 is a schematic illustration of a real-time visual indication of propagation velocities, in accordance with some examples of the present disclosure.

Reference is now made to FIG. 11, which is a schematic illustration of probe 26 and anatomical surface 42, in accordance with some examples of the present disclosure.

As described above with reference to FIGS. 1-2, the LATs at measurement locations 44 are calculated by the processor based on signals acquired by electrodes 28, which belong to probe 26. In some examples, the processor further computes the respective propagation velocities (or at least the propagation directions) at at least some of measurement locations 44 in real-time, i.e., while the electrodes are at the measurement locations. (In other words, in real-time, the processor treats at least some of measurement locations 44 as sampling locations 45, and hence computes the propagation velocities at these measurement locations, without using a digital model of the anatomical surface.)

For example, the propagation velocities may be computed once per cardiac cycle. This real-time computation may be performed as described above with reference to FIGS. 2-4, alternatively or additionally to the model-based computation described above.

Reference is now made to FIG. 12, which is a schematic illustration of a real-time visual indication of propagation velocities, in accordance with some examples of the present disclosure.

Subsequently to each real-time computation of propagation velocities, the processor indicates the velocities. Typically, to indicate the directions of electrical propagation, the processor displays an icon 26' of the probe and places, at portions 28' of the icon corresponding to those of the electrodes located at the sampling locations for which the directions were computed, respective markers 117 oriented in the directions of electrical propagation. (For simplicity, markers 117 are shown in FIG. 12 only for a small number of electrodes.) In some examples, prior to indicating the directions of electrical propagation, the processor smooths the directions, as described above with reference to FIG. 9A.

Typically, the processor varies at least one property (e.g., a color, shape, length, or thickness) of the markers in accordance with the speeds of electrical propagation. For example, the markers may have (i) a first shape and a first thickness for those of the speeds that belong to a first range (e.g., for those of the speeds greater than $v_{T3}$), (ii) the first shape and a second thickness for those of the speeds that belong to a second range that is lower than the first range (e.g., for those of the speeds less than $v_{T3}$ but greater than a lower threshold $v_{T4}$), and (iii) a second shape for those of the speeds that belong to a third range that is lower than the second range (e.g., for those of the speeds less than $v_{T4}$). FIG. 12 shows such an example, whereby (i) a first marker 117a includes a longer, thinner arrow, indicating a normal propagation speed, (ii) a second marker 117b includes a shorter, thicker arrow, indicating a slower propagation speed, and (iii) a third marker 117c includes a circle, indicating electrically-inactive tissue. (Typically, to avoid false markings, electrically-inactive tissue is marked only if it is known that the relevant electrode is contacting the tissue.)

Optionally, another property of the markers may be varied in accordance with the LATs. For example, the markers may be colored in accordance with a color scale based on the LATs.

As shown in FIG. 12, the icon of the probe may be overlaid over an image 42" of the anatomical surface that is being mapped. Alternatively, the icon may be overlaid over the surface of a model. In some examples, the display of the icon and markers is refreshed multiple times per cardiac cycle, so as to account for movement of the probe during the cardiac cycle.

Optimal Selection of Bipolar Voltages

Figures 13, 14:
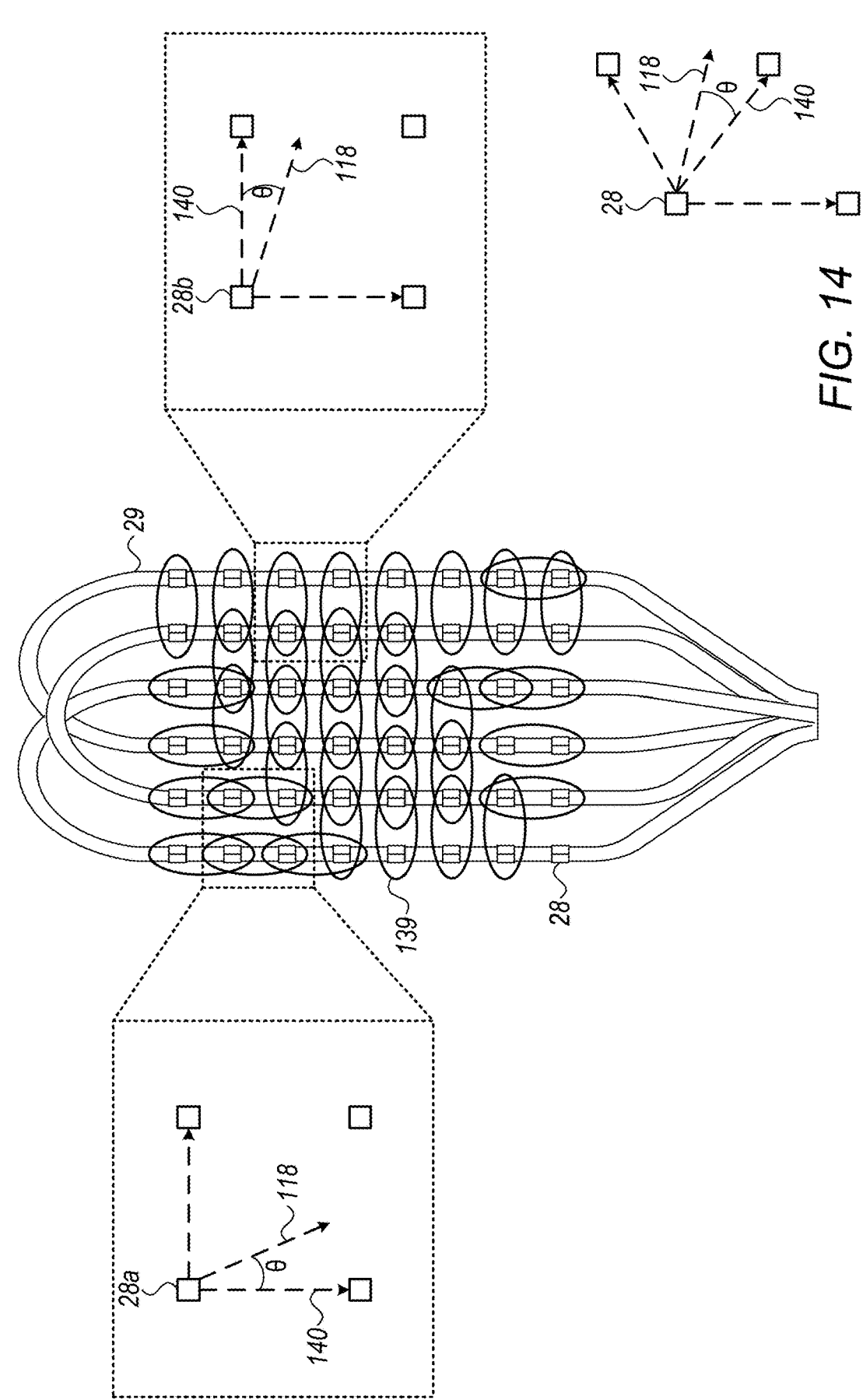
FIGS. 13-14 are schematic illustrations of a method for selecting bipolar voltages, in accordance with some examples of the present disclosure.

Reference is now made to FIG. 13, which is a schematic illustration of a method for selecting pairs of electrodes for bipolar voltage measurements, in accordance with some examples of the present disclosure.

In some examples, subsequently to computing the respective directions of electrical propagation at the locations of electrodes 28, the processor selects pairs 139 of adjacent ones of the electrodes such that, for each pair 139, a vector 140 joining the pair to one another is aligned, to within a predefined threshold degree of alignment, with the direction of electrical propagation at the location of one of the electrodes belonging to the pair. (Thus, the pair selection is based on the propagation direction, rather than the propagation speed.) Subsequently to selecting the pairs of electrodes, the processor associates respective bipolar voltages measured by the pairs of electrodes with model 38 (FIG. 1). Thus, advantageously, less-relevant bipolar voltages are omitted from the model.

For a rectangular grid of electrodes as shown in FIG. 13, in which the distance between adjacent (or "neighboring") electrodes in the same row is the same as the distance between adjacent rows, the threshold degree of alignment is generally 45°. For each of the electrodes (excluding, typically, one of the corner electrodes), the processor decides whether to pair the electrode with an adjacent electrode in the same row, to pair the electrode with an adjacent electrode in an adjacent row, or not to pair the electrode at all. In particular, for each of the potentially pairable adjacent electrodes, the processor calculates the angle θ between vector 140, which points from the electrode to the adjacent electrode (or vice versa), and another vector 118 oriented in the propagation direction. If θ (or |180°−θ|) is less than the threshold angle, the adjacent electrode is paired with the electrode.

(Typically, only a single adjacent electrode in the same row is potentially pairable, this electrode always being to the left of, or always being to the right of, the electrode for which a pair is sought. Similarly, typically, only a single adjacent electrode in an adjacent row is potentially pairable, the adjacent row always being above, or always being below, the electrode for which a pair is sought. Thus, no pair of electrodes is selected more than once.)

Thus, in the example shown in FIG. 13, a first electrode 28a is paired with the adjacent electrode lying below electrode 28a in the same column, while a second electrode 28b is paired with the adjacent electrode in the column to the right of second electrode 28b.

Reference is now further made to FIG. 14, which shows the method of FIG. 13 for hexagonal arrangements of electrodes, in accordance with some examples of the present disclosure.

In some examples, as described in U.S. application Ser. No. 17/092,627, whose disclosure is incorporated herein by reference, electrodes 28 are arranged in a hexagonal grid, such that each electrode is spaced equidistantly from up to six neighboring electrodes. For example, the rows of electrodes on splines 29 (FIG. 13) may be staggered with respect to each other. In such examples, the threshold degree of alignment is generally 30°, and the processor considers up to three adjacent electrodes for pairing.

Figure 15:
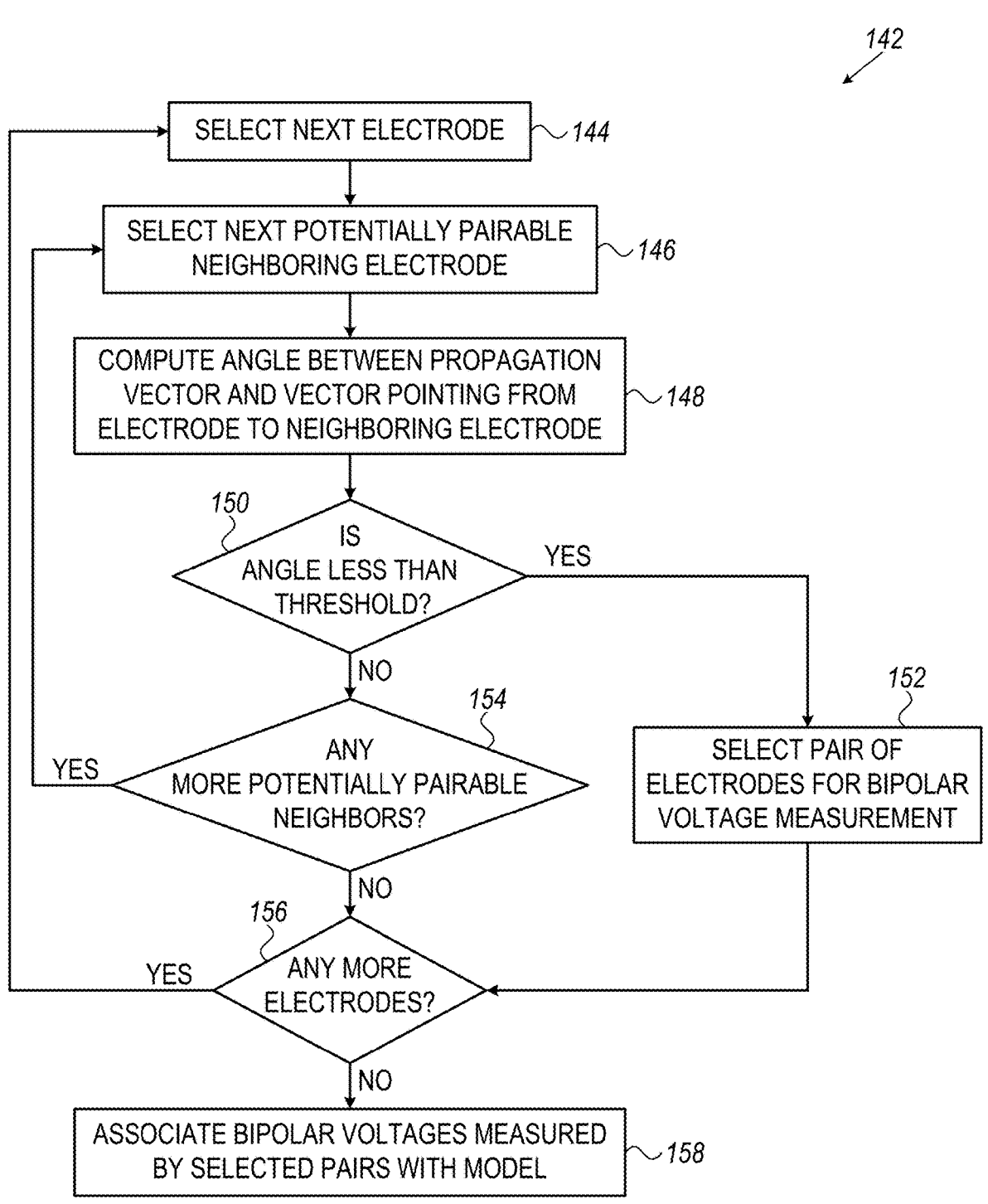
FIG. 15 is a flow diagram for an algorithm for selecting pairs of electrodes for bipolar voltage measurements, in accordance with some examples of the present disclosure.

For further details, reference is now made to FIG. 15, which is a flow diagram for an algorithm 142 for selecting pairs of electrodes for bipolar voltage measurements, in accordance with some examples of the present disclosure.

Typically, algorithm 142 is executed at least once, e.g., exactly once, per cardiac cycle. Per algorithm 142, each of the electrodes (excluding, typically, one of the corner electrodes, which does not have any potentially pairable neighbors) is selected at an electrode-selecting step 144. Following the selection of the electrode, a potentially pairable neighboring electrode (e.g., the right neighbor or lower neighbor of the selected electrode) is selected at a neighbor-selecting step 146. Next, the processor, at an angle-computing step 148, computes the angle θ (FIGS. 13-14) for the pair of electrodes (i.e., the selected electrode and its selected neighbor).

Subsequently to computing θ, the processor ascertains, at an angle-comparing step 150, whether θ (or |180°−θ|) is less than the threshold angle (e.g., 45° or 30°). If yes, the pair of electrodes are selected for bipolar voltage measurement (i.e., the bipolar voltage between the pair is selected for association with model 38 (FIG. 5)) at a pair-selecting step 152. Otherwise, the processor checks, at a checking step 154, whether any potentially pairable neighbors have not yet been selected. If yes, the processor returns to neighbor-selecting step 146 and selects the next potentially pairable neighbor.

Subsequently to performing pair-selecting step 152 or ascertaining that no potentially pairable neighbors remain to be selected, the processor checks, at a checking step 156, whether any electrodes remain to be selected. If yes, the processor returns to electrode-selecting step 144 and selects the next electrode. Otherwise, the processor, at a model-augmenting step 158, associates the bipolar voltages measured by the selected pairs of electrodes with model 38 (FIG. 5). For example, the processor may color surface 42' of the model in accordance with a color scale that ranges over the bipolar voltages. Alternatively or additionally, in response to movement of a mouse pointer over a point on surface 42', or to a clicking of the mouse on the point, the processor may display an indication of the electrode pair from which the bipolar voltage at the point was acquired, and/or the bipolar voltage signal itself.

Enhanced LAT Computation

Figure 16:
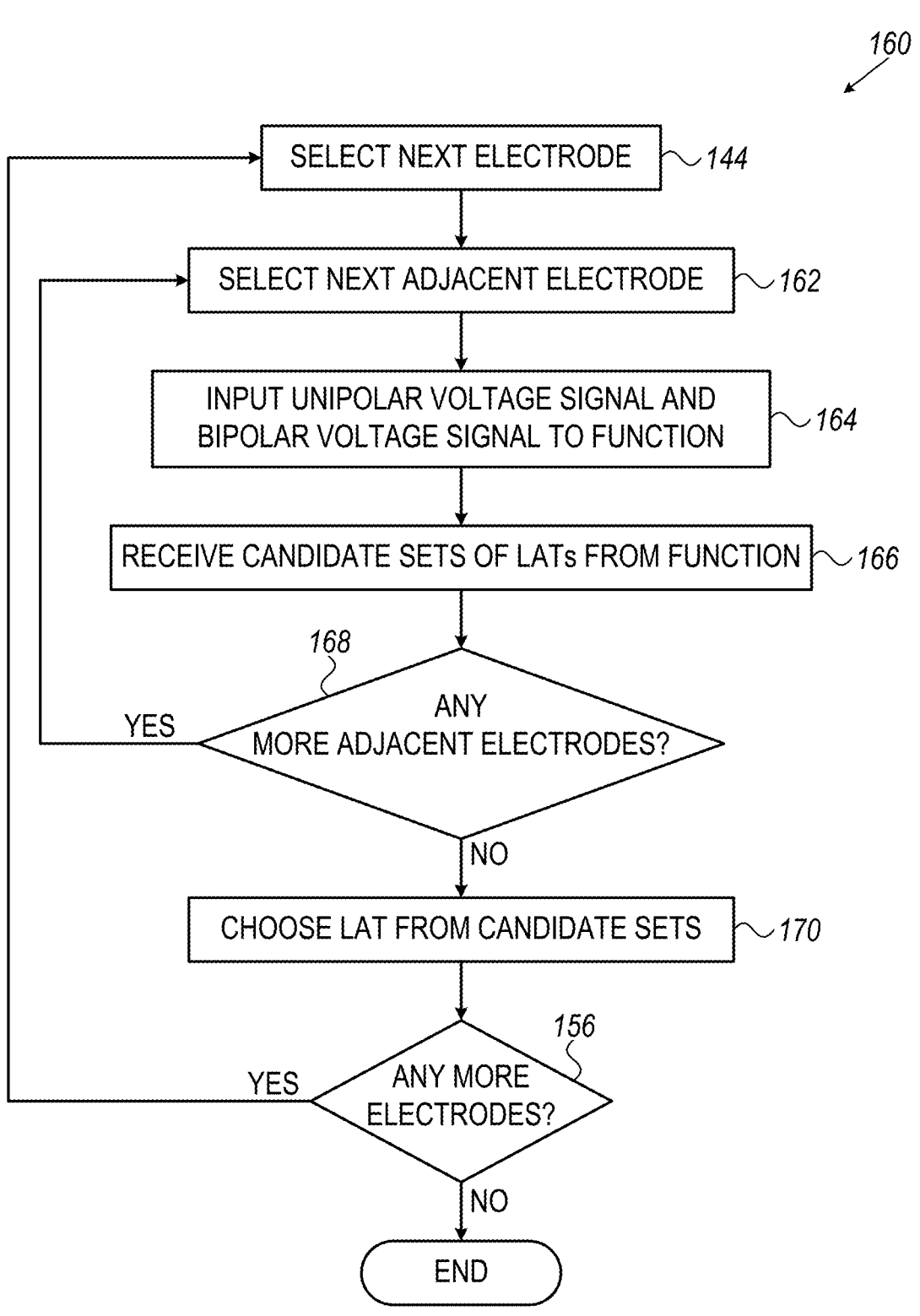
FIG. 16 is a flow diagram for an algorithm for computing the respective LATs at locations of electrodes, in accordance with some examples of the present disclosure.

Reference is now made to FIG. 16, which is a flow diagram for an algorithm 160 for computing the respective LATs at the locations of the electrodes, in accordance with some examples of the present disclosure. Algorithm 160 may be executed by the processor at any time during the electroanatomical mapping procedure.

By way of introduction, it is noted that algorithm 160 utilizes a function configured to return a candidate set of LATs for any location, based on a unipolar voltage signal and a bipolar voltage signal acquired from the location. Such functions are described, for example, in U.S. Pat. No. 9,380,953 to Houben et al., whose disclosure is incorporated herein by reference.

Each iteration of algorithm 160 begins with electrode-selecting step 144, at which the processor selects an electrode E1 belonging to the probe. Following the selection of E1, the processor selects an electrode E2 that neighbors (i.e., is adjacent to) E1, at a neighbor-selecting step 162. The processor then inputs two signals to the aforementioned function at a signal-inputting step 164: a unipolar voltage signal, which represents the unipolar voltage between E1 and a reference electrode, and a bipolar voltage signal, which represents the bipolar voltage between E1 and E2. Subsequently, at an output-receiving step 166, the processor receives, as output from the function, a candidate set of LATs computed by the function based on the input. For example, the output may include the unipolar voltage signal with annotations marking the candidate LATs.

Subsequently, the processor checks, at a checking step 168, whether E1 has any more neighboring electrodes. If yes, the processor returns to neighbor-selecting step 162 and selects the next neighbor of E1. Otherwise, the processor, at a LAT-choosing step 170, chooses a LAT from all the candidate sets that were received. For example, the processor may choose the candidate LAT at which the derivative of the unipolar signal is greatest, relative to the other candidate LATs.

Thus, for example, given a rectangular grid of electrodes in which each electrode has up to four equidistant neighbors, the processor may choose the LAT from up to four candidate sets. Given a hexagonal arrangement in which each electrode has up to six equidistant neighbors, the processor may choose the LAT from up to six candidate sets.

EXAMPLES

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A system (20) includes a display (36) and a processor (32), configured to obtain multiple local activation times (LATs) at different respective measurement locations (44) on an anatomical surface (42) of a heart (24). The processor (32) is further configured to compute respective directions of electrical propagation at one or more sampling locations (45) on the anatomical surface (42), by, for each sampling location (45) of the sampling locations, selecting a respective subset of the measurement locations (44) for the sampling location (45), constructing a set of vectors, each of at least some of the vectors including, for a different respective measurement location (44) in the subset, three position values derived from respective position coordinates of the measurement location (44) and an LAT value derived from the LAT at the measurement location (44), and computing the direction of electrical propagation at the sampling location (45) based on a Principal Component Analysis (PCA) of a 4×4 covariance matrix for the set of vectors. The processor (32) is further configured to indicate the directions of electrical propagation on the display (36).

Example 2

The system (20) according to Example 1, wherein the processor (32) is configured to construct the set of vectors by:

computing a scaling factor based on a variance of the LATs across the subset of the measurement locations (44), and for each measurement location (44) in the subset:
  scaling, by the scaling factor, a parameter selected from
    the group of parameters consisting of: the position
    coordinates of the measurement location (44), and the
    LAT at the measurement location, and
  constructing the vector corresponding to the measurement
    location (44) from the scaled parameter.

Example 3

The system (20) according to any one of Examples 1-2,
wherein the processor (32) is configured to compute the
direction of electrical propagation at the sampling location
(45) by projecting a first principal component of the cova-
riance matrix onto respective dimensions of the position
coordinates.

Example 4

The system (20) according to any one of Examples 1-3,
wherein the processor (32) is further configured to compute
a speed of electrical propagation at each of the sampling
locations (45), by:
  for a hypothetical line (47) passing through the sampling
  location (45) and oriented in the direction of electrical
  propagation at the sampling location (45), computing
  respective distances along the line (47) at which lie respec-
  tive projections, onto the line (47), of the subset of the
  measurement locations (44), and
    computing the speed as a slope of a regression function
    (51) fitted to a group of regression points (49), each of which
    includes, for a different respective measurement location
    (44) belonging to the subset, (i) the distance along the line
    (47) at which the projection of the measurement location
    (44) lies, and (ii) the LAT at the measurement location (44).

Example 5

The system (20) according to any one of Examples 1-4,
wherein the processor (32) is further configured to smooth
the directions of electrical propagation prior to indicating the
directions of electrical propagation.

Example 6

The system (20) according to any one of Examples 1-5,
wherein the processor (32) is configured to select the respec-
tive subset of the measurement locations (44) for the sam-
pling location (45) by:
  identifying those of the measurement locations (44) that
  are within a predefined distance of the sampling location
  (45), and
    selecting the subset of the measurement locations (44)
    from the identified measurement locations (44).

Example 7

The system according to Example 6, wherein the proces-
sor is configured to select the subset by:
  for each measurement location within the predefined
  distance of the sampling location:
    computing a propagation-speed estimate, which estimates
      a propagation speed between the sampling location and
      the measurement location, and
    provided the propagation-speed estimate exceeds a pre-
      defined speed-estimate threshold, selecting the mea-
      surement location.

Example 8

The system according to Example 7, wherein the proces-
sor is further configured to compute an interpolated LAT for
the sampling location, and wherein the processor is config-
ured to compute the propagation-speed estimate based on
the interpolated LAT.

Example 9

The system according to Example 8,
  wherein the predefined speed-estimate threshold is a first
predefined speed-estimate threshold and the propagation-
speed estimate is a first propagation-speed estimate, and
  wherein the processor is configured to compute the inter-
polated LAT by:
  clustering those of the measurement locations within the
    predefined distance of the sampling location into one or
    more clusters such that, for each of the clusters, for
    each pair of measurement locations in the cluster, a
    second propagation-speed estimate, which estimates a
    propagation speed between the pair of measurement
    locations, exceeds a second predefined speed-estimate
    threshold,
  based on respective distances between the sampling loca-
    tion and the clusters, identifying one of the clusters, and
  computing the interpolated LAT as a weighted average of
    the LATs at at least some of the measurement locations
    in the identified one of the clusters.

Example 10

The system (20) according to any one of Examples 1-9,
  wherein the measurement locations (44) correspond to
different respective measurement points (44') on a digital
model surface (42') representing the anatomical surface (42),
the measurement points (44') being associated with the
LATs, respectively,
  wherein the processor (32) is further configured to des-
ignate, on the digital model surface (42'), a plurality of
sampling points (45'), and
  wherein the sampling locations (45) correspond to the
sampling points (45'), respectively.

Example 11

The system (20) according to Example 10, wherein the
processor (32) is configured to indicate the directions of
electrical propagation by displaying the model surface (42')
with respective markers (116) overlaying the model surface
(42') at the sampling points (45') and oriented in the direc-
tions of electrical propagation, respectively.

Example 12

The system (20) according to Example 11, wherein the
processor (32) is further configured to:
  compute respective speeds of electrical propagation at the
sampling locations (45), and
  vary at least one property of the markers (116) in accor-
dance with the speeds.

Example 13

The system (20) according to any one of Examples 11-12,
wherein the processor (32) is further configured to, prior to displaying the model surface (42') with the markers (116) overlaying the model surface (42'):

> iteratively:
>
> recompute the directions of electrical propagation, and
>
> shift the sampling points (45') toward each other in response to the directions of electrical propagation.

Example 14

The system according to any one of Examples 1-9, wherein the processor is configured to obtain the LATs by calculating the LATs based on signals acquired by respective electrodes belonging to an intrabody probe, wherein the sampling locations include at least some of the measurement locations, and wherein the processor is configured to indicate the directions of electrical propagation while the electrodes are at the measurement locations, respectively.

Example 15

The system according to Example 14, wherein the processor is configured to indicate the directions of electrical propagation by:

> displaying an icon of the probe, and
>
> placing, at portions of the icon corresponding to those of the electrodes located at the sampling locations, respective markers oriented in the directions of electrical propagation, respectively.

Example 16

The system according to Example 15, wherein the processor is further configured to:

> compute respective speeds of electrical propagation at the sampling locations, and
>
> vary at least one property of the markers in accordance with the speeds.

Example 17

A method includes obtaining multiple local activation times (LATs) at different respective measurement locations (44) on an anatomical surface (42) of a heart (24). The method further includes computing respective directions of electrical propagation at one or more sampling locations (45) on the anatomical surface (42), by, for each sampling location (45) of the sampling locations, selecting a respective subset of the measurement locations (44) for the sampling location (45), constructing a set of vectors, each of at least some of the vectors including, for a different respective measurement location (44) in the subset, three position values derived from respective position coordinates of the measurement location (44) and an LAT value derived from the LAT at the measurement location (44), and computing the direction of electrical propagation at the sampling location (45) based on a Principal Component Analysis (PCA) of a 4×4 covariance matrix for the set of vectors. The method further includes indicating the directions of electrical propagation on a display (36).

Example 18

The method according to Example 17, wherein constructing the set of vectors includes:

> computing a scaling factor based on a variance of the LATs across the subset of the measurement locations (44); and
>
> for each measurement location (44) in the subset:
>
> scaling, by the scaling factor, a parameter selected from the group of parameters consisting of: the position coordinates of the measurement location (44), and the LAT at the measurement location (44), and
>
> constructing the vector corresponding to the measurement location (44) from the scaled parameter.

Example 19

The method according to any one of Examples 17-18, wherein computing the direction of electrical propagation at the sampling location (45) includes computing the direction of electrical propagation by projecting a first principal component of the covariance matrix onto respective dimensions of the position coordinates.

Example 20

The method according to any one of Examples 17-19, further including computing a speed of electrical propagation at each of the sampling locations (45), by:

> for a hypothetical line (47) passing through the sampling location (45) and oriented in the direction of electrical propagation at the sampling location (45), computing respective distances along the line (47) at which lie respective projections, onto the line (47), of the subset of the measurement locations (44), and
>
> computing the speed as a slope of a regression function (51) fitted to a group of regression points (49), each of which includes, for a different respective measurement location (44) belonging to the subset, (i) the distance along the line (47) at which the projection of the measurement location (44) lies, and (ii) the LAT at the measurement location (44).

Example 21

The method according to any one of Examples 17-20, wherein the measurement locations (44) correspond to different respective measurement points (44') on a digital model surface (42') representing the anatomical surface (42), the measurement points (44') being associated with the LATs, respectively, wherein the method further includes designating, on the digital model surface (42'), a plurality of sampling points (45'), and wherein the sampling locations (45) correspond to the sampling points (45'), respectively.

Example 22

A system includes an electrical interface and a processor. The processor is configured to receive, via the electrical interface, respective signals acquired by a plurality of electrodes on an anatomical surface of a heart. The processor is further configured to compute, based on the signals, respective local activation times (LATs) at respective locations of the electrodes. The processor is further configured to compute, based on the LATs, respective directions of electrical propagation at the locations. The processor is further configured to select pairs of adjacent ones of the electrodes such that, for each of the pairs, a vector joining the pair is aligned, to within a predefined threshold degree of alignment, with the direction of electrical propagation at the location of one of the electrodes belonging to the pair. The processor is further configured to associate respective bipolar voltages measured by the pairs of electrodes with a digital model of the anatomical surface.

Example 23

The system according to Example 22, wherein the processor is configured to compute the LAT at the location of each first electrode of the electrodes by:

obtaining multiple candidate sets of LATs for the location, by, for each second electrode of the electrodes that is adjacent to the first electrode:

providing, as input to a function, (i) a unipolar voltage signal, which represents a unipolar voltage between the first electrode and a reference electrode, and (ii) a bipolar voltage signal, which represents a bipolar voltage between the first electrode and the second electrode, and receiving, as output from the function, a respective one of the candidate sets, and choosing the LAT from the candidate sets.

Example 24

A method includes, based on respective signals acquired by a plurality of electrodes on an anatomical surface of a heart, computing respective local activation times (LATs) at respective locations of the electrodes. The method further includes, based on the LATs, computing respective directions of electrical propagation at the locations. The method further includes selecting pairs of adjacent ones of the electrodes such that, for each of the pairs, a vector joining the pair is aligned, to within a predefined threshold degree of alignment, with the direction of electrical propagation at the location of one of the electrodes belonging to the pair. The method further includes associating respective bipolar voltages measured by the pairs of electrodes with a digital model of the anatomical surface.

Example 25

The method according to Example 24, wherein computing the LATs comprises computing the LAT at the location of each first electrode of the electrodes by:

obtaining multiple candidate sets of LATs for the location, by, for each second electrode of the electrodes that is adjacent to the first electrode:

providing, as input to a function, (i) a unipolar voltage signal, which represents a unipolar voltage between the first electrode and a reference electrode, and (ii) a bipolar voltage signal, which represents a bipolar voltage between the first electrode and the second electrode, and receiving, as output from the function, a respective one of the candidate sets; and choosing the LAT from the candidate sets.

Example 26

A computer software product includes a tangible non-transitory computer-readable medium in which program instructions are stored. The instructions, when read by a processor, cause the processor to receive respective signals acquired by a plurality of electrodes on an anatomical surface of a heart, to compute, based on the signals, respective local activation times (LATs) at respective locations of the electrodes, to compute, based on the LATs, respective directions of electrical propagation at the locations, to select pairs of adjacent ones of the electrodes such that, for each of the pairs, a vector joining the pair is aligned, to within a predefined threshold degree of alignment, with the direction of electrical propagation at the location of one of the electrodes belonging to the pair, and to associate respective bipolar voltages measured by the pairs of electrodes with a digital model of the anatomical surface.

Example 27

A system includes a display and a processor. The processor is configured to compute, based on respective signals acquired by a plurality of electrodes, which belong to an intrabody probe, on an anatomical surface of a heart, respective local activation times (LATs) at respective locations of the electrodes. The processor is further configured to compute, based on the LATs, respective directions of, and speeds of, electrical propagation at the locations. The processor is further configured to display an icon of the probe on the display while the electrodes are at the locations, respectively. The processor is further configured to place, at portions of the icon corresponding to the electrodes, respective markers oriented in the directions of electrical propagation, respectively, and having at least one property that varies in accordance with the speeds.

Example 28

The system according to Example 27, wherein the processor is configured to compute the LAT at the location of each first electrode of the electrodes by:

obtaining multiple candidate sets of LATs for the location, by, for each second electrode of the electrodes that is adjacent to the first electrode:

providing, as input to a function, (i) a unipolar voltage signal, which represents a unipolar voltage between the first electrode and a reference electrode, and (ii) a bipolar voltage signal, which represents a bipolar voltage between the first electrode and the second electrode, and receiving, as output from the function, a respective one of the candidate sets, and choosing the LAT from the candidate sets.

Example 29

The system according to any one of Examples 27-28, wherein the property varies in accordance with the speeds by virtue of the markers:

having a first shape and a first thickness for those of the speeds that belong to a first range, having the first shape and a second thickness for those of the speeds that belong to a second range that is lower than the first range, and having a second shape for those of the speeds that belong to a third range that is lower than the second range.

Example 30

The system according to Example 29, wherein the markers have at least one other property that varies in accordance with the LATs.

Example 31

The system according to Example 30, wherein the markers are colored in accordance with a color scale based on the LATs.

Example 32

A method includes, based on respective signals acquired by a plurality of electrodes, which belong to an intrabody probe, on an anatomical surface of a heart, computing respective local activation times (LATs) at respective locations of the electrodes. The method further includes, based on the LATs, computing respective directions of, and speeds of, electrical propagation at the locations. The method further includes, while the electrodes are at the locations, respectively, displaying an icon of the probe. The method further includes placing, at portions of the icon corresponding to the electrodes, respective markers oriented in the directions of electrical propagation, respectively, and having at least one property that varies in accordance with the speeds.

Example 33

The method according to Example 32, wherein computing the LATs comprises computing the LAT at the location of each first electrode of the electrodes by:
obtaining multiple candidate sets of LATs for the location, by, for each second electrode of the electrodes that is adjacent to the first electrode:
providing, as input to a function, (i) a unipolar voltage signal, which represents a unipolar voltage between the first electrode and a reference electrode, and (ii) a bipolar voltage signal, which represents a bipolar voltage between the first electrode and the second electrode, and
receiving, as output from the function, a respective one of the candidate sets; and choosing the LAT from the candidate sets.

Example 34

The method according to any one of Examples 32-33, wherein the property varies in accordance with the speeds by virtue of the markers:
having a first shape and a first thickness for those of the speeds that belong to a first range,
having the first shape and a second thickness for those of the speeds that belong to a second range that is lower than the first range, and
having a second shape for those of the speeds that belong to a third range that is lower than the second range.

Example 35

The method according to Example 34, wherein the markers have at least one other property that varies in accordance with the LATs.

Example 36

The method according to Example 35, wherein the markers are colored in accordance with a color scale based on the LATs.

Example 37

A computer software product includes a tangible non-transitory computer-readable medium in which program instructions are stored. The instructions, when read by a processor, cause the processor to compute, based on respective signals acquired by a plurality of electrodes, which belong to an intrabody probe, on an anatomical surface of a heart, respective local activation times (LATs) at respective locations of the electrodes. The instructions further cause the processor to compute, based on the LATs, respective directions of, and speeds of, electrical propagation at the locations. The instructions further cause the processor to display an icon of the probe while the electrodes are at the locations, respectively. The instructions further cause the processor to place, at portions of the icon corresponding to the electrodes, respective markers oriented in the directions of electrical propagation, respectively, and having at least one property that varies in accordance with the speeds.

It will be appreciated by persons skilled in the art that the present disclosure is not limited to what has been particularly shown and described hereinabove. Rather, the scope of the present disclosure includes both combinations and sub-combinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:
1. A system, comprising:
a display; and
a processor, configured to:
obtain multiple local activation times (LATs) at different respective measurement locations on an anatomical surface of a heart,
compute respective directions of electrical propagation at one or more sampling locations on the anatomical surface, by, for each sampling location of the sampling locations:
selecting a respective subset of the measurement locations for the sampling location,
constructing a set of vectors, each of at least some of the vectors including, for a different respective measurement location in the subset, three position values derived from respective position coordinates of the measurement location and an LAT value derived from the LAT at the measurement location, and
computing the direction of electrical propagation at the sampling location based on a Principal Component Analysis (PCA) of a 4×4 covariance matrix for the set of vectors, and
indicate the directions of electrical propagation on the display.
2. The system according to claim 1, wherein the processor is configured to construct the set of vectors by:
computing a scaling factor based on a variance of the LATs across the subset of the measurement locations, and
for each measurement location in the subset:
scaling, by the scaling factor, a parameter selected from the group of parameters consisting of: the position coordinates of the measurement location, and the LAT at the measurement location, and constructing the vector corresponding to the measurement location from the scaled parameter.

3. The system according to claim 1, wherein the processor is configured to compute the direction of electrical propagation at the sampling location by projecting a first principal component of the covariance matrix onto respective dimensions of the position coordinates.

4. The system according to claim 1, wherein the processor is further configured to compute a speed of electrical propagation at each of the sampling locations, by:

for a hypothetical line passing through the sampling location and oriented in the direction of electrical propagation at the sampling location, computing respective distances along the line at which lie respective projections, onto the line, of the subset of the measurement locations, and computing the speed as a slope of a regression function fitted to a group of regression points, each of which includes, for a different respective measurement location belonging to the subset, (i) the distance along the line at which the projection of the measurement location lies, and (ii) the LAT at the measurement location.

5. The system according to claim 1, wherein the processor is further configured to smooth the directions of electrical propagation prior to indicating the directions of electrical propagation.

6. The system according to claim 1, wherein the processor is configured to select the respective subset of the measurement locations for the sampling location by:

identifying those of the measurement locations that are within a predefined distance of the sampling location, and selecting the subset of the measurement locations from the identified measurement locations.

7. The system according to claim 1, wherein the measurement locations correspond to different respective measurement points on a digital model surface representing the anatomical surface, the measurement points being associated with the LATs, respectively, wherein the processor is further configured to designate, on the digital model surface, a plurality of sampling points, and wherein the sampling locations correspond to the sampling points, respectively.

8. The system according to claim 7, wherein the processor is configured to indicate the directions of electrical propagation by displaying the model surface with respective markers overlaying the model surface at the sampling points and oriented in the directions of electrical propagation, respectively.

9. The system according to claim 8, wherein the processor is further configured to:

compute respective speeds of electrical propagation at the sampling locations, and vary at least one property of the markers in accordance with the speeds.

10. The system according to claim 8, wherein the processor is further configured to, prior to displaying the model surface with the markers overlaying the model surface:

iteratively:

recompute the directions of electrical propagation, and shift the sampling points toward each other in response to the directions of electrical propagation.

11. A method, comprising:

obtaining multiple local activation times (LATs) at different respective measurement locations on an anatomical surface of a heart;

computing respective directions of electrical propagation at one or more sampling locations on the anatomical surface, by, for each sampling location of the sampling locations:

selecting a respective subset of the measurement locations for the sampling location, constructing a set of vectors, each of at least some of the vectors including, for a different respective measurement location in the subset, three position values derived from respective position coordinates of the measurement location and an LAT value derived from the LAT at the measurement location, and computing the direction of electrical propagation at the sampling location based on a Principal Component Analysis (PCA) of a 4×4 covariance matrix for the set of vectors; and indicating the directions of electrical propagation on a display.

12. The method according to claim 11, wherein constructing the set of vectors comprises:

computing a scaling factor based on a variance of the LATs across the subset of the measurement locations; and for each measurement location in the subset:

scaling, by the scaling factor, a parameter selected from the group of parameters consisting of: the position coordinates of the measurement location, and the LAT at the measurement location, and constructing the vector corresponding to the measurement location from the scaled parameter.

13. The method according to claim 11, wherein computing the direction of electrical propagation at the sampling location comprises computing the direction of electrical propagation by projecting a first principal component of the covariance matrix onto respective dimensions of the position coordinates.

14. The method according to claim 11, further comprising computing a speed of electrical propagation at each of the sampling locations, by:

for a hypothetical line passing through the sampling location and oriented in the direction of electrical propagation at the sampling location, computing respective distances along the line at which lie respective projections, onto the line, of the subset of the measurement locations, and computing the speed as a slope of a regression function fitted to a group of regression points, each of which includes, for a different respective measurement location belonging to the subset, (i) the distance along the line at which the projection of the measurement location lies, and (ii) the LAT at the measurement location.

15. The method according to claim 11, further comprising, prior to indicating the directions of electrical propagation, smoothing the directions of electrical propagation.

16. The method according to claim 11, wherein selecting the respective subset of the measurement locations for the sampling location comprises:

identifying those of the measurement locations that are within a predefined distance of the sampling location; and selecting the subset of the measurement locations from the identified measurement locations.

17. The method according to claim 11, wherein the measurement locations correspond to different respective measurement points on a digital model surface representing the anatomical surface, the measurement points being associated with the LATs, respectively, wherein the method further comprises designating, on the digital model surface, a plurality of sampling points, and wherein the sampling locations correspond to the sampling points, respectively.

18. The method according to claim 17, wherein indicating the directions of electrical propagation comprises indicating the directions of electrical propagation by displaying the model surface with respective markers overlaying the model surface at the sampling points and oriented in the directions of electrical propagation, respectively.

19. The method according to claim 18, further comprising:

computing respective speeds of electrical propagation at the sampling locations; and varying at least one property of the markers in accordance with the speeds.

20. The method according to claim 18, further comprising, prior to displaying the model surface with the markers overlaying the model surface:

iteratively:

recomputing the directions of electrical propagation, and shifting the sampling points toward each other in response to the directions of electrical propagation.

\* \* \* \* \*